United States Patent
Rubio et al.

(10) Patent No.: US 7,354,773 B2
(45) Date of Patent: Apr. 8, 2008

(54) METHOD AND APPARATUS FOR PREPARING CELL SAMPLES FOR INTRACELLULAR ANTIGEN DETECTION USING FLOW CYTOMETRY

(75) Inventors: Oilda Rubio, Miami, FL (US); Carlos Aparicio, Miami, FL (US); John A. Maples, Miami, FL (US); Julie Wilkinson, Fort Lauderdale, FL (US); Cecilia Smith, Miami, FL (US); Frank J. Lucas, Boca Raton, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 624 days.

(21) Appl. No.: 10/437,695

(22) Filed: May 14, 2003

(65) Prior Publication Data

US 2004/0229368 A1    Nov. 18, 2004

(51) Int. Cl.
*G01N 1/18* (2006.01)

(52) U.S. Cl. .......... 436/177; 435/2; 435/7.25; 435/40.5; 435/366; 435/372; 435/398; 435/400; 435/401; 435/287.2; 435/971; 436/521; 436/522; 436/536; 436/538; 436/546; 436/17; 436/45; 436/47

(58) Field of Classification Search ......... 436/18, 436/56, 63, 64, 165, 169, 175, 176, 177, 436/178, 517, 518, 521, 522, 523, 538, 546, 436/17, 536, 45, 47, 161, 166, 172; 435/2, 435/6, 7.1, 7.2, 7.24, 7.25, 7.92, 398, 400, 435/401, 285.2, 287.2, 287.7, 971, 973, 366, 435/372, 40.5

See application file for complete search history.

(56) References Cited

U.S. PATENT DOCUMENTS

| | | | | |
|---|---|---|---|---|
| 5,686,261 A | * | 11/1997 | Zhang et al. | 435/40.5 |
| 6,495,333 B1 | * | 12/2002 | Willmann et al. | 435/7.24 |
| 6,692,968 B2 | * | 2/2004 | Burshteyn et al. | 436/63 |
| 6,828,157 B1 | * | 12/2004 | Pankowsky | 436/176 |
| 2002/0123154 A1 | | 9/2002 | Burshteyn et al. | |

FOREIGN PATENT DOCUMENTS

EP      1116037 B1      5/2004

* cited by examiner

*Primary Examiner*—Gailene R. Gabel
(74) *Attorney, Agent, or Firm*—Warren W. Kurz; Mitchell E. Alter

(57) ABSTRACT

A method and apparatus for preparing biological cell samples for intracellular analysis. The invention is based upon the recognition that many of the steps of the conventional methods for such sample preparation can be eliminated, leading to a process that readily lends itself to automation and the advantages associated therewith. The method of the invention comprises the steps of (a) cell-fixation, (b) permeabilization and (c) staining (or labeling) of intracellular molecules of interest by probes that are readily detectable by flow cytometric techniques, all without any intervening cell-washing (and re-suspension) steps. Rather, the single cell-washing step is effected after these three steps have been carried out. Preferably, the washing step is carried out by passing the fixed, permeabilized and stained cell sample through a semi-permeable membrane that serves to filter out (by transmission) interferants to waste while retaining the cells of interest.

12 Claims, 23 Drawing Sheets

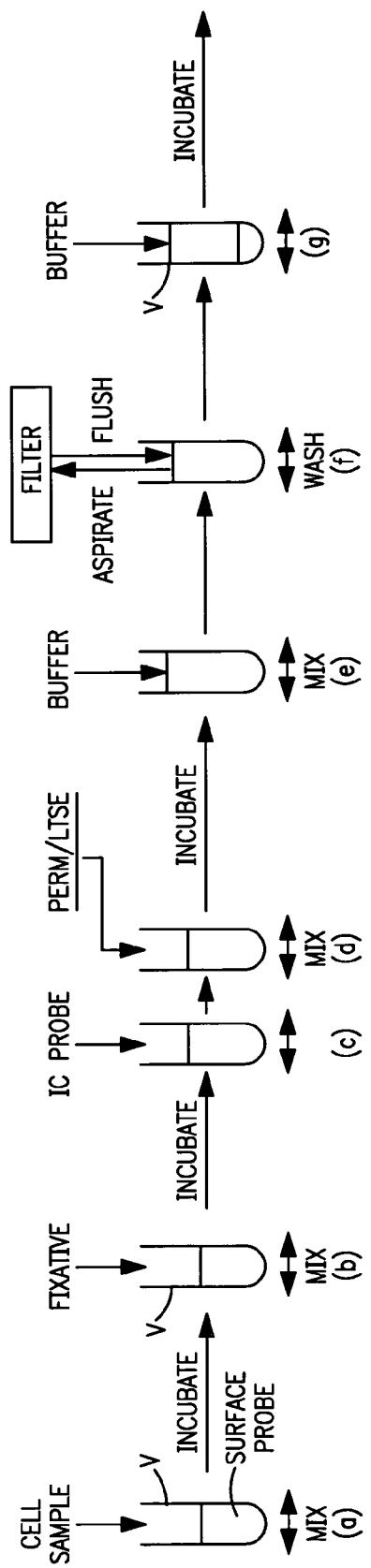
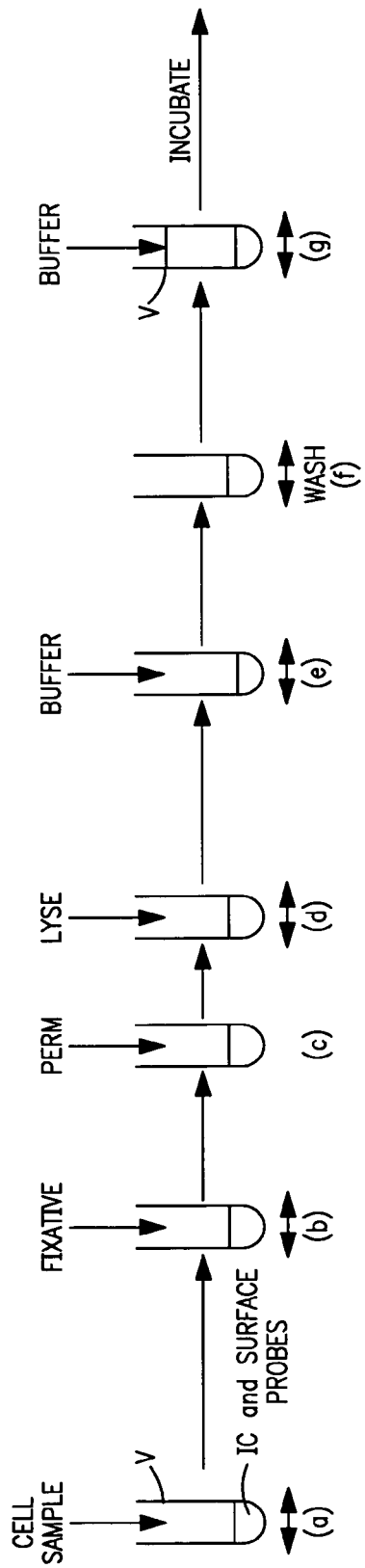
FIG. 2A
FIG. 2B

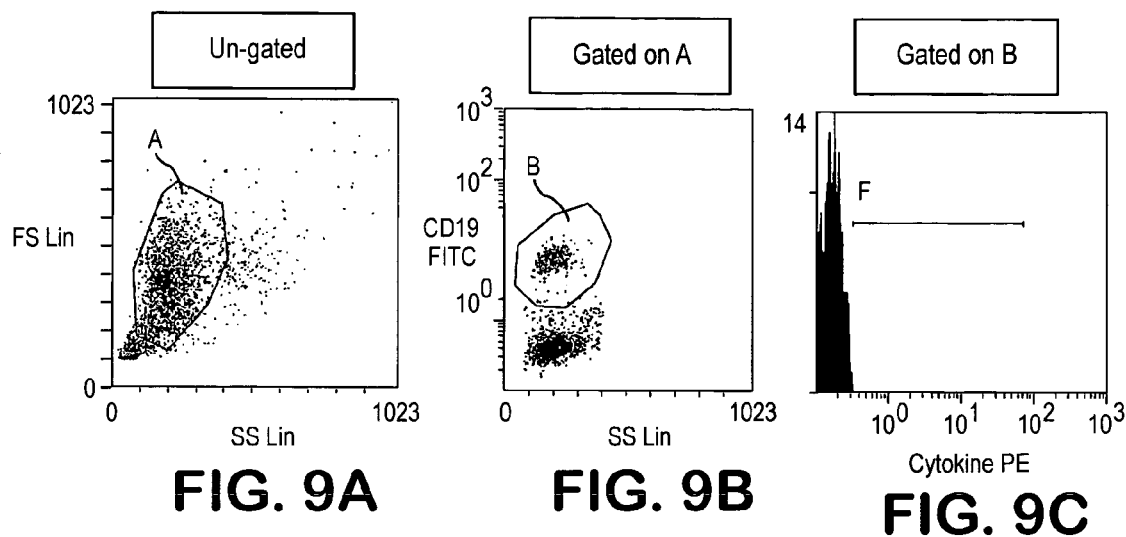
FIG. 9A  FIG. 9B  FIG. 9C
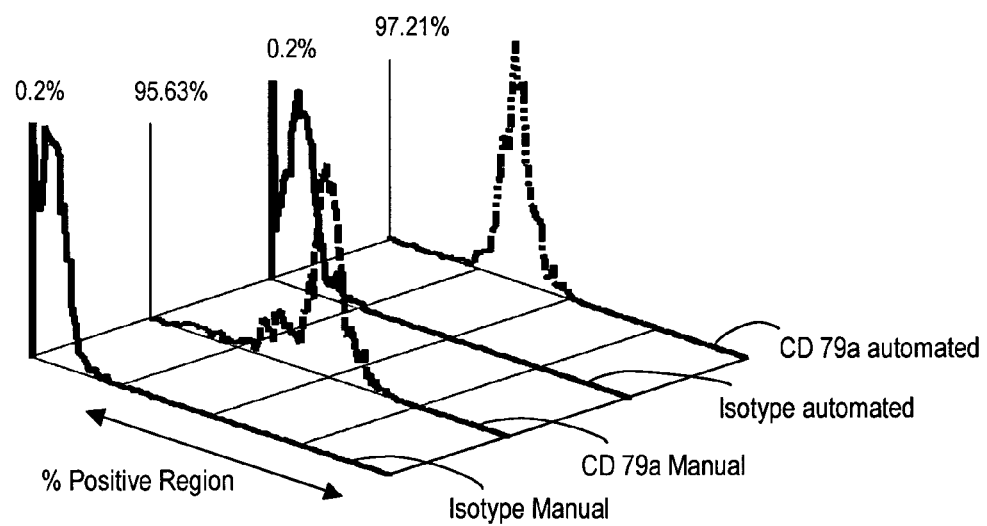
FIG. 9D

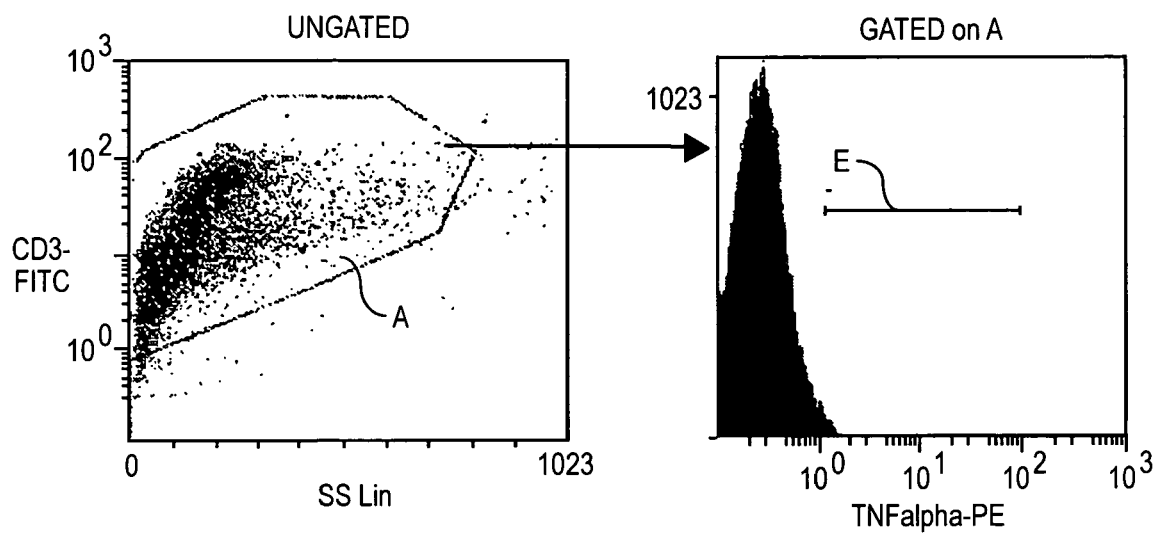
FIG. 13A  FIG. 13B
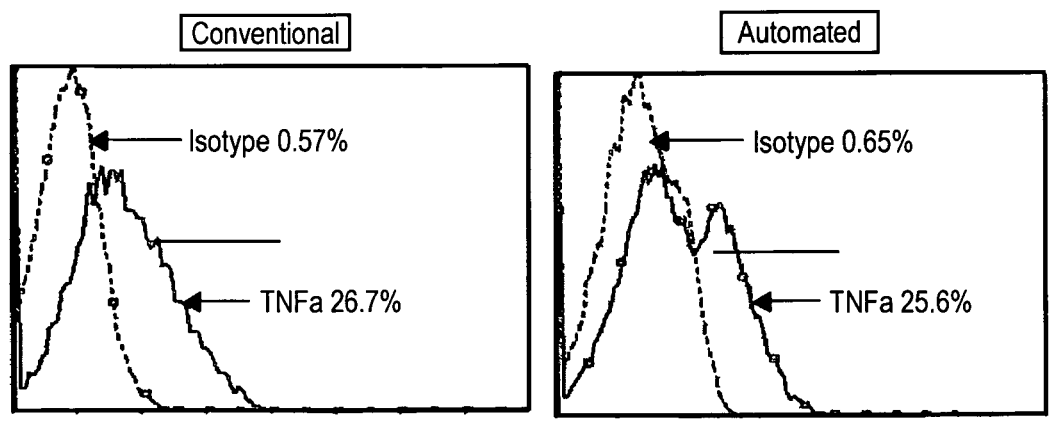
FIG. 13C  FIG. 13D

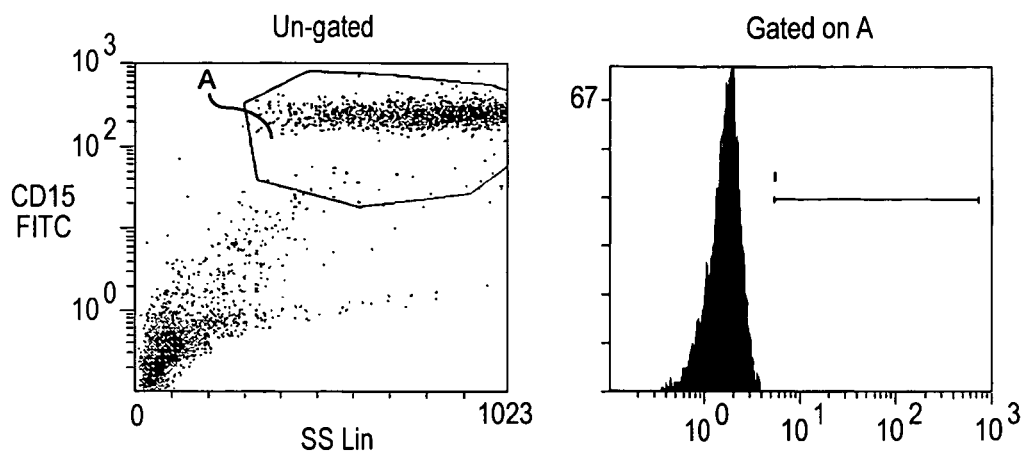
FIG. 14A
FIG. 14B
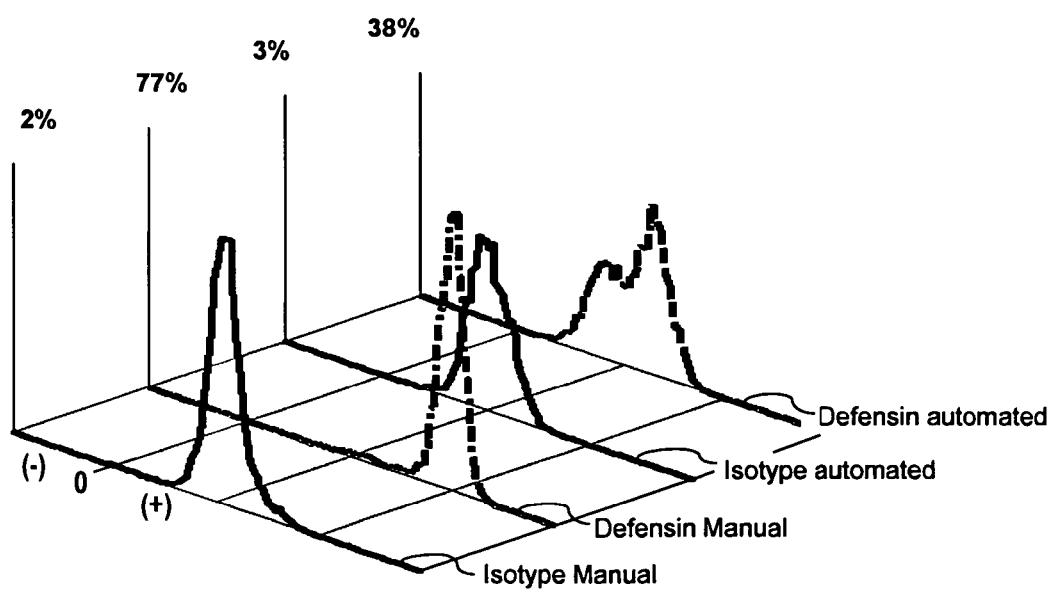
FIG. 14C

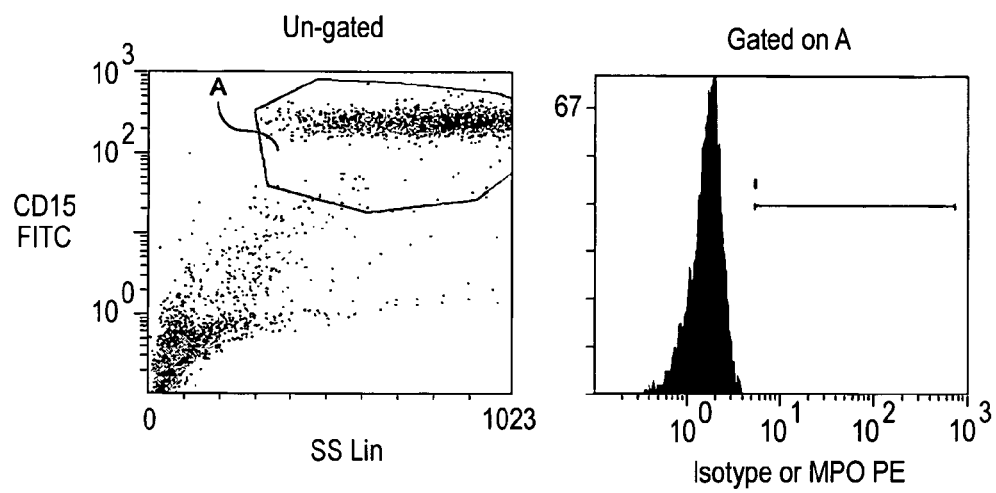
FIG. 15A  FIG. 15B
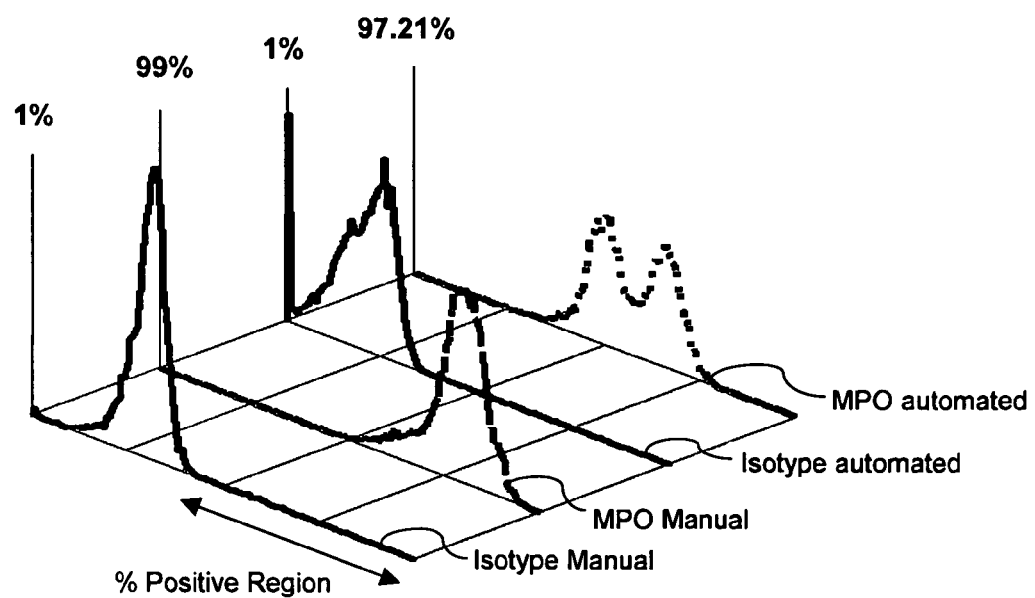
FIG. 15C

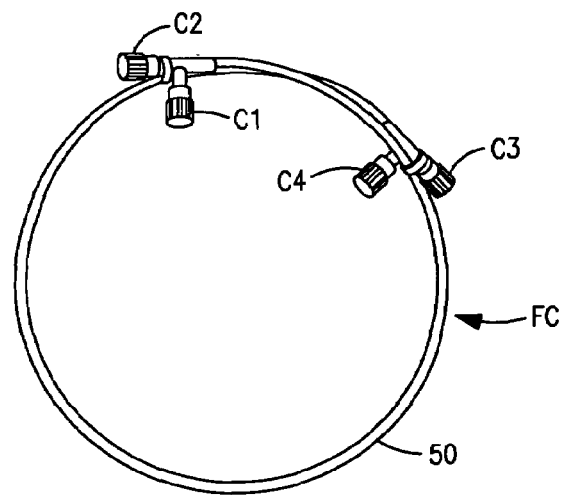
FIG. 21A
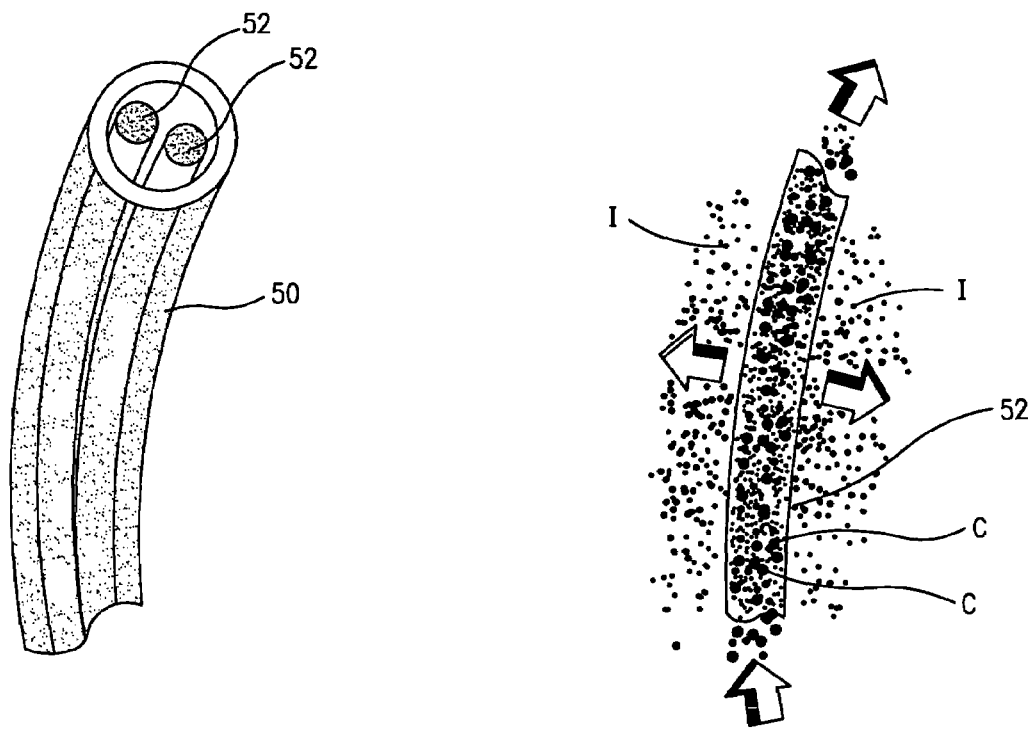
FIG. 21B
FIG. 21C

METHOD AND APPARATUS FOR PREPARING CELL SAMPLES FOR INTRACELLULAR ANTIGEN DETECTION USING FLOW CYTOMETRY

BACKGROUND OF THE INVENTION

1. Field of the Invention

The present invention relates to improvements in methods and apparatus for preparing cell samples, e.g., human blood samples, for intracellular assay using flow cytometric techniques.

2. Discussion of the Prior Art

Cell surface immunophenotyping using fluorescent flow cytometry has become a relatively routine process for differentiating and counting cells of interest in a cell sample containing many different cell types. Typically, cell surface probes, e.g., fluorochrome-labeled monoclonal antibodies (MABs) or other suitably labeled ligands, specific to antigens on the outer surface of the cells of interest, are used to selectively tag or "stain" such cells for subsequent detection. The flow cytometer operates to detect the stained cells by irradiating individual cells in the sample, one-by one, with radiation specially adapted to excite the fluorochrome labels. When irradiated, the labels fluoresce and their associated cells scatter the incident radiation in a pattern determined by the physical and optical characteristics of the irradiated cell. Suitable photo-detectors within the flow cytometer detect the scattered radiation and fluorescence, and their respective output signals are used to differentiate the different cell types on the basis of their respective light-scattering and fluorescence signatures.

The process for preparing samples for cell surface immunophenotyping is relatively simple. Basically, the cell surface probes are mixed with the cell sample, and the resulting mixture is incubated for a time sufficient to enable the probes to bind to the cells of interest. Thereafter, if the cell sample is a whole blood sample, the tagged cell sample may be lysed to eliminate red blood cells. Optionally, the tagged cell sample may be washed to eliminate interferants, e.g., unattached probes, cell fragments and other debris that may interfere with the detection of the cells of interest. While such sample preparation is often performed manually, automated sample preparation instruments are commercially available for facilitating the sample-preparation process. These instruments are advantageous in that they remove many potential human errors and other variations from the sample-preparation steps they perform, thereby providing more repeatable results. Such automated instruments include, for example, various pipetting instruments that operate under the control of a suitably programmed microprocessor to automatically pipet and dispense precise volumes of sample and reagent materials (e.g., cell-surface markers) into one or more reaction vessels or tubes where the materials are mixed together (e.g., by vibration or vortex mixing). One such instrument is the PrepPlus2™ Sample Prep Instrument made and sold by Beckman Coulter, Inc., Miami, Fla. Other stand-alone instruments that facilitate the sample-preparation process for cell surface immunophenotyping are those that operate to lyse a whole blood sample, e.g. the Q-Prep™ Sample Prep Work Station line of instruments sold by Beckman Coulter, and those that, in effect, wash the sample to eliminate interferants and cellular debris that adversely effect the detection of the cells of interest within the sample. Such sample washing instruments include various centrifuging instruments, as well as the CellPrep™ Cell Washer, also sold by Beckman Coulter, Inc. The latter instrument operates to filter a cell sample presented to it using a microporous (i.e., semi-permeable) hollow fiber membrane, as described in detail in the commonly assigned U.S. Pat. Disclosure No. 2002/0123154 A1 in the names of Burshteyn et al., published on Sep. 5, 2002.

In addition to the many different stand-alone, sample-preparing instruments that are adapted to automatically perform different portions of a cell sample preparation process for cell surface immunophenotyping, there are some flow cytometers that operate to automatically carry out all of the requisite sample preparation steps within the environs of the flow cytometer itself. See, for example, the Cell Dyne™ 4000 Blood Analyzer made by Abbott Laboratories, and the R-1000 Reticulocyte Analyzer made by Toa Electronics. Both of these instruments are capable of providing hematology and fluorescent flow cytometry results on a cell sample prepared within the measuring instrument. Note, in the latter instrument, cell samples containing reticulocytes are prepared for flow cytometery analysis by mixing the cells sample with a fluorescent stain that is selectively absorbed through the reticulocyte membrane and taken up by the RNA contained by such membrane. In neither of these instruments is the cell sample washed prior to passing the sample through an optical flow cell for analysis.

While cell sample preparation may be regarded as a relatively simple matter in the case of cell surface immunophenotyping and, thus, is readily susceptible to a certain degree of automation, the process for preparing cell samples for intracellular assays is considerably more complex. Such assays, of course, require access to the cell interior so that the intracellular antigens or molecules of interest, e.g., cytokines, chemokines, defensins, effector molecules, etc., can be tagged for identification. Since the probes normally used to tag intracellular antigens and molecules for identification on a flow cytometer are relatively large in size, usually being in the form of a ligand/fluorochrome conjugate, the sample preparation process must include a permeabilization step by which correspondingly large openings are created in the cell membrane to enable passage of these probes into the cell interior. (Note, while reticulocyte assays of the type noted above may be viewed as an intracellular assay in that the reticulocyte's internal RNA, an intracellular antigen, is tagged to identify the reticulocyte, preparation of cell samples for this assay do not require any special pre-processing (e.g. permeabilizing) in order for the relatively small fluorescent dye molecules used to tag the RNA to pass through the pores of the cell membrane and thereby gain access to the RNA within the cell.)

In addition to the need to permeabilize the cell membrane, the sample-preparation process for intracellular assays also requires that cell membranes and contents of the cell be "fixed" prior to the permeabilization step in order to maintain the integrity of the membrane during permeabilization and to prevent the intracellular material from diffusing out of the cells after permeabilization. This fixing step also serves to preserve the localization of the intracellular antigens of interest so that they are more readily accessible to the probes that are about to enter the cells. It will be appreciated that the fixation step cannot be so severe as to (a) prevent the probes from entering the cell membrane, (b) prevent the probes from gaining access to the intracellular antigens of interest, or (c) alter the confirmation of the antigen to the extent that it is unrecognizable by the probe.

A further complicating factor to the intracellular sample-preparation process is the need to ultimately produce a sample that is virtually free of interferants or contaminants that may act to raise the background level against which the antigens of interest is to be detected. It will be appreciated that many intracellular antigens are present in very low amounts within a cell and thus require correspondingly low, substantially interferant-free, background levels to detect. Further, the intracellular antigens of interest are sometimes found in a very low percentage of the cells comprising the analysis sample and thus may be regarded as "rare events." Hence, controlling the levels of all contaminants in the sample is critical to the accuracy and repeatability of such assays. Due to the need to both fix and permeabilize the cells of interest in preparation for an intracellular assay, the sample-preparation process, as practiced heretofore, has always required multiple wash steps for eliminating the aforementioned interferants that can compromise the detection of the intracellular antigens of interest.

To date, each of the above-noted cell-washing steps associated with the conventional intracellular sample-preparation process has been carried out with a centrifuge. Upon adding a buffer solution to the sample vessel to increase its volume, the sample is spun down at a relatively high g force (e.g., 300-500 g) to produce a concentrated pellet of the cells of interest. A portion of the remaining supernatant containing the interferants and the like is then carefully poured off, and the remaining supernatant is used to re-suspend the sample cells. Rigorous vortex mixing is then necessary to disperse the individual cells of the pellet. While this method of washing cells may be considered as highly effective in physically separating the cells of interest from the soluble components within the reaction vessel, there are some obvious disadvantages associated with centrifugation. For example, it is well known that the removal of any supernatant resulting from a centrifugation process can result in a significant loss in the total number of cells in the sample, or may result in a selective loss of certain cell types. Also, the centrifugation apparatus itself is often relatively bulky and requires substantial laboratory space to accommodate it. Further, in the case of separating permeabilized cells from interferants by centrifugation, there are additional problems. For example, it is known that permeabilized cells become more buoyant as a result of the permeabilizing process; further, the cells also become sticky and tend to clump together. This increase in buoyancy requires centrifugation at greater g forces and for longer periods of time to achieve the desired pelleting. The increased g forces, coupled with the stickier permeabilized membranes, make re-suspension of the individual cells even more difficult. Worse yet, the increased g force can disrupt the cell membrane and the entire cell will be lost.

As may be appreciated from the discussion above, the conventional process for preparing cell samples for intracellular assaying is relatively complex and, owing to its complexity, it is routinely performed manually in a variety of ways. Referring to FIG. 1, the typical conventional process may be summarized as follows: First, a predetermined volume of cell surface markers (e.g., suitably labeled monoclonal antibodies) is added to a predetermined volume of a cell sample (e.g., a whole blood sample) in a reaction vessel. The surface markers are intended to identify, by means of flow cytometry, those cells in which intracellular antigens or molecules are to be assayed. After gently mixing the blood sample and cell surface makers and incubating the mixture for a predetermined time and at a desired temperature (e.g., room temperature), a predetermined volume of a cell-fixing reagent (e.g., a formaldehyde solution) is added. Upon mixing the fixative with the blood sample, which can be achieved by either introducing the fixative into the vessel at a predetermined rate, or by vortexing the fixative and sample after adding the fixative at a much slower rate, the resulting mixture is incubated again. As indicated above, the incubation time and fixative strength are critical to achieve the desired degree of fixation. Thereafter, the fixed sample is washed via centrifugation to rid the sample of interferants. To prepare the sample for centrifugation (washing), an excess of (e.g., 20-fold) buffer solution (e.g., a phosphate-buffered saline solution) is added. The buffer has the effect of quenching the fixing action of the fixative, diluting interfering reagents, and increasing the sample volume to a level suitable for centrifugation. The sample is then transferred to a centrifuge where it is spun down to produce a relatively concentrated pellet of cells covered by a liquid supernatant containing interferants. Upon removing the reaction vessel from the centrifuge and carefully removing (to avoid the loss of cells of interest) most of the supernatant, the remaining materials are subjected to a rigorous vortex mixing, preferably carried out on a suitable mixing instrument, to disperse and re-suspend the cells of the pellet. Then, the intracellular probes (e.g. MAB's with fluorochrome labels) can be added, followed by a predetermined volume of a permeabilizing/lysing reagent (e.g., saponin), or vice versa. After a gentle mixing step, the probes and permeabilizing/lysing reagent are incubated with the fixed sample cells for a predetermined time, and another relatively large volume of buffer is added to quench the permeabilizing and lysing action, to dilute the interfering reagents and to increase the sample volume to a level suitable for another centrifugation. Upon centrifuging the sample again, removing the supernatant and re-suspending the pelleted cells by adding another volume of buffer and vortex mixing the sample, the cell sample is now ready to be transported to the flow cytometer for analysis.

From the above, it will be appreciated that the conventional process for preparing cell samples for intracellular assaying on a flow cytometry is subject to considerable error and non-repeatability. No matter how precise the protocol for carrying out this relatively complex and lengthy process, the need for human involvement can lead to huge variations in the sample produced. Any variations in timing or techniques in aspirating, mixing and dispensing the samples and reagents, either from day-to-day by the same technician, or from technician-to-technician, or from laboratory-to-laboratory, can result in meaningless data, especially in light of the relative rarity or dimness of the events being assayed. Further, the potential for cell loss and cell damage during each of the multiple centrifugation (wash) steps and vortex mixing steps are obvious disadvantages to the present sample preparation process. Clearly, there is a need for a simpler process, one with substantially fewer steps, and one that lends itself to total automation.

SUMMARY OF THE INVENTION

In view of the foregoing discussion, an object of this invention is to provide a new and improved method for preparing cell samples for intracellular assay on a flow cytometer, a method that is considerably less complex than the afore-described prior art method, and a method that better lends itself to automation and to the various advantages inherent in such automation.

Another object of this invention is to provide a fully automated apparatus or instrument system for preparing a biological cell sample for analysis of intracellular molecules contained by cells of interest within the cell sample.

According to one aspect of the invention, a new and improved method for preparing a biological cell sample for an intracellular assay is provided. Unlike the above-described prior art methods that require multiple cell-washing (i.e., centrifugation) steps, each necessitating transport of the sample to and from the centrifugation apparatus and subsequent vortex mixing to re-suspend the cell sample so as to able to proceed to the next step of the sample-preparing process, the method of the invention uses but a single wash step, that occurring at the very end of the process, after all the sample and reagent-pipetting and incubations steps have been carried out in the same reaction vessel. According to the invention, the steps of cell-fixing, permeabilization, lysing (if desired), cell-surface staining (if necessary), and intracellular antigen-staining are carried out, not necessarily in that order, in the same reaction vessel and without any intervening cell-washing step. Only after the cell sample has been fixed, permeabilized/lysed, and stained to label intracellular antigens or molecules of interest, is the cell sample finally washed to eliminate interferants (e.g., cell debris and unattached probes) that hinder the detection of the intracellular molecules of interest. Preferably, such cell washing step is achieved by a filtration technique rather than by centrifugation. As a result, the sample-preparing method of the invention can be readily automated.

According to a preferred embodiment, a method for preparing a cell sample for intracellular analysis comprises the steps of:

a) mixing in a reaction vessel a predetermined volume of a biological cell sample with a predetermined volume of a stabilizing reagent, such reagent being adapted to enhance the integrity of a cellular membrane of at least certain cells of interest within the biological cell sample and to preserve the localization of certain intracellular molecules of interest within such cells of interest;

b) incubating the biological cell sample with the stabilizing reagent for a predetermined time to provide a stabilized cell sample;

c) adding to the stabilized cell sample a predetermined volume of at least one intracellular probe that is specific to the intracellular molecules of interest within the cells of interest;

d) mixing the stabilized cell sample and probe with a predetermined volume of a permeabilizing reagent adapted to permeabilize the cellular membrane of the cells of interest;

e) incubating for a predetermined time the stabilized biological cell sample with the intracellular probe and the permeabilizing reagent to permeabilize the cellular membrane of the cells of interest and to allow the intracellular probe to bind with, and thereby label, the intracellular molecules of interest;

f) adding to the reaction vessel a predetermined volume of a diluting reagent adapted to dilute the cells of interest therein and to reduce the rate of permeabilization of the cellular membrane, thereby forming a diluted sample containing the labeled intracellular molecules within the cells of interest; and g) washing the diluted sample to rid such sample of interferants that may have been produced in the sample in carrying out steps a) through h).

Preferably, the washing step is effected by removing the diluted sample from the reaction vessel and filtering it through a semi-permeable membrane that is adapted to transmit the diluting reagent, as well as any unattached probes and other interferants in the diluted sample, while preventing the cells of interest from passing through the membrane, whereby a filtered sample containing the labeled intracellular molecules within the cells of interest is provided. Preferably, the filtered sample is then returned to the same reaction vessel in a buffer solution, thereby providing a diluted and filtered sample adapted for analysis of the cells containing the labeled intracellular molecules.

Compared to the afore-described prior art method for preparing cell samples for intracellular assay, it will be apparent that the method of the invention provides a prepared cell sample by carrying out far fewer steps and, most importantly, only a single wash step is required at the end of the process. When the cells are washed using a preferred filtering process, as described herein, the cells of interest are less inclined to become damaged or selectively lost by the washing process, as often occurs in the centrifugation step of the prior art, as well as in the vortex mixing step used to re-suspend the cells from the pellet formed by centrifugation.

According to a second aspect of the present invention, an automated instrument system is provided for automatically carrying out the entire cell sample preparation method of the invention. According to a first preferred embodiment, such instrument system comprises: a) a stand-alone pipetting/incubating component selectively operable to pipette predetermined volumes of reagent materials from a supply of such materials into each of a plurality of reaction vessels containing a cell sample, and to incubate mixtures of cell sample and reagent materials in the reaction vessels at a predetermined temperature and for a predetermined time to provide processed cell sample in which predetermined intracellular molecules within certain cells of interest have been labeled for detection on a flow cytometer; b) a stand alone cell washing component selectively operable to separate the cells of interest within a processed cell sample presented thereto from interferants and debris that would tend to impair the flow cytometric detection of the intracellular molecules of interest; c) a reaction vessel-transport component selectively operable to effect the transport of reaction vessels from the pipetting/incubating component to the cell washing component; and d) logic and control means for coordinating the operation of components a) through c). According to a preferred embodiment, the cell washer comprises a tubular member having a semi-permeable wall through which cell debris and other interferants may pass but not the cells of interest. The cell washer further comprises a pipetting apparatus for drawing the cell sample, including interferants, out of the reaction vessel and into the tubular member, so that the cells of interest are trapped in the tubular member and the interferants pass through its semi-permeable wall under the vacuum force of the pipetting apparatus. The cell washer further includes a diluting component for simultaneously advancing the trapped cells in the tubular member to the initial or another reaction vessel, and for re-suspending the trapped cells in a buffer for subsequent analysis. According to a second preferred embodiment, the above components of the automated instrument system are embodied in a single platform instrument.

Being adapted to repeatedly and precisely carry out the entire sample preparation method of the invention without any human involvement, the automated apparatus of the invention provides multiple samples in which i) the coefficient of variation (CV) is significantly lower than that of the labor-intensive prior art method for producing a like number of samples, and ii) the results are far more reproducible.

The invention and its advantages will be better understood from the ensuing detailed description of preferred embodiments, reference being made to the accompanying drawings in which like reference characters denote like parts.

BRIEF DESCRIPTION OF THE DRAWINGS

FIGS. 2A and 2B illustrate the steps of cell sample preparation methods in accordance with two preferred embodiments of the invention;

FIG. 3A through FIG. 19C are scattergrams and graphs illustrating the effectiveness of the methods described in the various Examples provided;

FIGS. 21A-C illustrate a hollow fiber cartridge; and

DETAILED DESCRIPTION OF PREFERRED EMBODIMENTS

Figure 1:
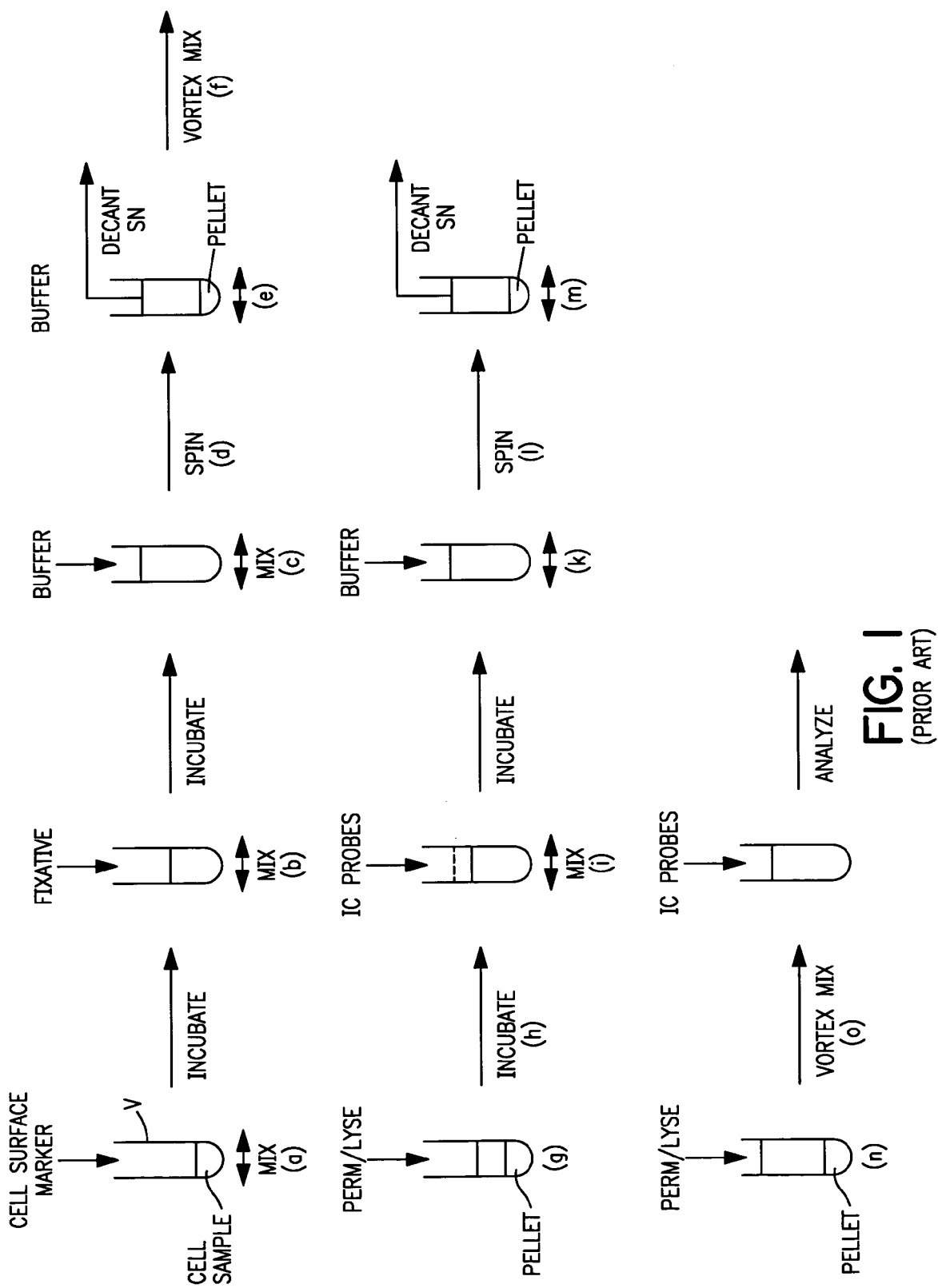
FIG. 1 illustrates the steps of a typical prior art method for preparing a cell sample for an intracellular assay on a conventional flow cytometer.

An important focus of cell-based research is to define distinct cell populations in the hopes of identifying the specific cells responsible for causing or preventing disease processes. To date, many methods are used to compare native and perturbed cells in normal and disease states, to discover differences at the nucleic acid, protein, and cellular function levels. The ability to detect and quantitate intracellular molecules has greatly expanded our ability to characterize cells, and our knowledge of how a cell functions in response to its environment. DNA can be quantitated to measure the process cell division and to determine the rate of proliferation. RNA can be measured to monitor gene function. Tubulin, actin, and intermediate filaments are examples of molecules responsible for the shape, integrity, motility, and function of cells. Cytokeratin is present inside cells of epithelial origin, which is useful in identifying rare circulating tumor cells. Signal transduction, the process of transmitting signals received on the outer membrane of the cell to the DNA inside the nucleus, involves a multitude of molecules and is required for a cell to respond to its environment and for every cellular process, for example: proliferation, activation, dying, or being an effector.

Cells also release, or secrete, molecules which communicate to other cells or which exert an effect. For example, cytokines are a very important group of small proteins secreted by cells of the immune system to communicate with other cells, and granzyme-B is an example of a killing effector molecule secreted by cytotoxic T cells of the immune system. Typically, secreted molecules do not accumulate in detectable quantities within a cell, so they are measured extracellularly using an ELISA-type assay (Enzyme-Linked Immunosorbent Assay). This is not an acceptable method when studying a specific cell type within a heterogeneous cell population. Therefore, to measure these on a cellular level, the secretory pathways must be blocked in vitro with a protein transport inhibitor (e.g., Brefeldin-A, Monensin, Secramine or Nocodazole), as in the case of intracellular cytokine measurements.

As noted in the introductory portion hereof discussed with reference to FIG. 1, the prior art method for preparing cell samples for intracellular assaying on a flow cytometer is a relatively lengthy, complex and tedious process. Typically, it requires the performance of upwards of 14 active steps, which exclude the various incubations between steps. Being carried out by hand, it is difficult to consistently produce repeatable results by this method, even when carried out by the same laboratory technician on the same day using the same samples and reagents. Also, it is difficult to manually process relatively large samples at one time. Further, even when carried out precisely and in accordance with an accepted protocol, the conventional process includes steps that can be harmful to the individual cells and their respective contents (e.g., the rigorous centrifugation and vortex mixing steps). All this leads to uncertainty in the results produced. There is a need to do better.

Now in accordance with the present invention, a new and improved method is provided for preparing cell samples for intracellular analysis via flow cytometric techniques. As will become apparent from the ensuing description, this new method requires fewer steps than the conventional sample-preparing process described above. Very importantly, the method of the invention does not require the multiple wash steps, typically centrifuging and vortex-mixing steps, that are most detrimental to the production of uniform cell samples. Rather, the method of the invention requires but a single wash step at the end of the process. Only after the cell sample has been fixed, permeabilized/lysed, and stained to label intracellular antigens or molecules of interest, is the cell sample finally washed to eliminate interferants (e.g., cell debris and unattached probes) that hinder the detection of the intracellular molecules of interest.

Referring to FIG. 2A, a preferred method of the invention begins, in the same manner as that of the prior art, by mixing in a reaction vessel V, a predetermined volume of a cell sample with a predetermined volume of cell surface markers or "probes." The cell sample may comprise, for example, whole blood comprising certain cells of interest (e.g., various leukocytes, platelets, erythrocytes, etc.) containing intracellular molecules or antigens of interest; or the cell sample may be a cell line, or comprise tumor cells or infectious agents. The cell surface markers typically comprise fluorochrome-tagged monoclonal antibodies that are specific to certain antigens of interest carried on the surface of the cells of interest. (Note, this initial step serves, of course, to label specific cells in a cell sample containing various different types of cells, only some of which contain the intracellular molecules of interest. In the case where the initial cell sample consists of a cell line in which all cells may contain the intracellular molecules of interest, this initial step of cell surface labeling may not be required.) Preferably, the cell sample is introduced at a flow rate that effects mixing of the cell sample and the cell surface markers; otherwise, these materials are mixed by a gentle shaking or swirling action applied to the reaction vessel, as indicated by the double-headed arrow. Following an incubation period (e.g. 15 minutes) sufficient to enable conjugation of the surface probes to the cells of interest, a predetermined volume of fixative is added to the cell sample, as noted in step (b) of the drawing. As noted above, the fixative is designed to preserve the integrity of the cell during the permeabilization step that is to follow. Preferably, the fixative is a conventional formaldehyde-based reagent of the type used in the prior art process; however, in contrast with the prior art, the volume of the fixative is relatively small, preferably being only about 25% of the volume conventionally used. Following another incubation period that enable the fixative to achieve its intended function, a predetermined volume of intracellular probes (e.g., fluorochrome-tagged MAb's) is added to the reaction vessel, as shown in step (c). This addition is immediately followed by the addition of a predetermined volume of a permeabilizing/lysing reagent, as shown in step (d). Preferably, the permeabilizing/lysing reagent, which may comprise saponin or the like, is added at a flow rate sufficient to effect mixing of the vessel contents (i.e., the fixed and surface-labeled cell sample, the intracellular probe(s) and the permeabilization/lysing reagent). The vessel contents are then incubated for a period sufficient to enable (1) the fixed cells of interest to become permeabilized, (2) the red cells to be lysed (assuming the cell sample is a whole blood sample and the RBC's are not the cells containing the intracellular antigens of interest), and (3) the intracellular probes to bind with, and thereby label, the intracellular molecules of interest. Thereafter, a buffer is added to the reaction vessel, shown as step (e), in an amount sufficient to inhibit the effect of the perm/lyse reagent, and the contents of the reaction vessel are subjected to a wash step, step (f) that operates to remove interferants from the cell sample while preserving the cells of interest. While this wash step may be a conventional centrifugation wash step as described above with reference to the prior art method; more preferably, however, the wash step comprises the step of filtering the cell sample solution through a semi-permeable membrane adapted to transmit the interferants and dissolved materials within the cell sample while trapping the cells of interest. After this filtering step, the trapped or filtered cells are dispensed into the same reaction vessel (or a different one) where they are re-suspended in a predetermined volume of a fresh buffer solution that is added to the vessel, shown as step (g), as the filtered cells are flushed from the filter. Most preferably, the wash step is effected, as schematically shown, by aspirating the cell sample into a microporous hollow fiber comprising a cylindrical wall made from the afore-mentioned semi-permeable membrane, and drawing the interferants, dissolved and otherwise, radially through the fiber's cylindrical wall via a vacuum force applied to the fiber exterior. Thereafter, a diluent or buffer is caused to flow through and around the fiber, causing the trapped cells of interest to be simultaneously dispensed from the fiber and re-suspended to the awaiting reaction vessel. This filtering and dispensing process is best described in the above-noted published U.S. patent application Ser. No. 2002/0123154. Thus, according to this cell-washing technique, the step of adding a buffer to the filtered cell sample, step (g) in FIG. 2A, is performed as the filtered cells are flushed from the filter (i.e., step (g) is part of step (f). Whatever the wash method, the cell sample, with its intracellular labels and, optionally, cell surface labels, is now ready for transport to a flow cytometer for analysis.

In FIG. 2B, a variation of the above method is illustrated. Here, both surface and intracellular probes are added to the reaction vessel containing a cell sample prior to the addition of the fixative. After an incubation period to enable the surface probes to conjugate with certain cell surface antigens, a fixative is added to the cell sample and, after a gentle mixing, the mixture is incubated, as above. Then, a suitable permeabilizing reagent is added, immediately followed by a separate lysing reagent, preferably ammonium chloride. Following an incubation period to enable permeabilization of the cells of interest, lysing of the red cells, and labeling of the intracellular antigens of interest by the intracellular probes, the cell sample is washed, for the first and only time, to eliminate interferants. Upon re-suspending the washed cells in a buffer, the sample is ready for analysis.

From the description above, it will be appreciated that relatively simple methods for preparing a cell sample for intracellular analysis have been provided. Each of the new sample-preparation methods has about one-half the number of active steps as that of the prior art. It will be appreciated that, up until the final wash step, the entire process is carried out without any intervening wash steps and/or vortex mixing; that is, the fixative, the intracellular probes, optionally the lyse, and the permeabilizing reagents are added, one after the other, with none of the normal washing and vortex-mixing steps in between. That this process is useful at all in preparing cell samples for intracellular analysis was quite unexpected. It was envisioned that the various reagents would interfere with each other in terms of their respective effectiveness, leading to a sample that might have been unsuitable for flow-cytometric analysis. To the contrary, the sample prepared by the methods of the invention have been found to be as useful as the most carefully prepared samples prepared according to the prior art. Moreover, as explained below, the methods of the invention can be readily automated using suitably modified conventional instruments, such as the as the Beckman Coulter PrepPlus2 pipetting instrument and the CellPrep cell-washing instrument. When so automated, multiple samples can be produced in which the coefficient of variability (CV) is considerably improved over what can be achieved by the conventional manual process. A further advantage of the sample preparation method of the invention is that it enables cell surface probes to bind with surface antigens prior to a fixation process (which can either destroy the surface antigen or reduce the binding efficiency with the probe) while at the same time maintaining the ability to have the surface and intracellular probes present after the permeabilization process (such that antigens that have not been expressed on the cell surface yet, or have been prevented from being expressed, or have been down regulated from the surface to the intracellular compartments, will be detected.

The effectiveness of the method the invention vis-à-vis the prior art method described above is illustrated by the following Examples in which various types of cell samples (e.g., whole blood, Peripheral Blood Mononuclear Cells (PMBCs), cell lines) are processed to prepare them for flow-cytometric analysis to detect different intracellular molecules of interest (e.g., B-cell antigen receptor complexes, cytokines, defensins, Cytoplasmic Proliferation Antigens (CPAs), vimentin, tubulin, cytokeratin, enzymes (e.g. MPO), etc.).

EXAMPLE 1

Figure 3A:
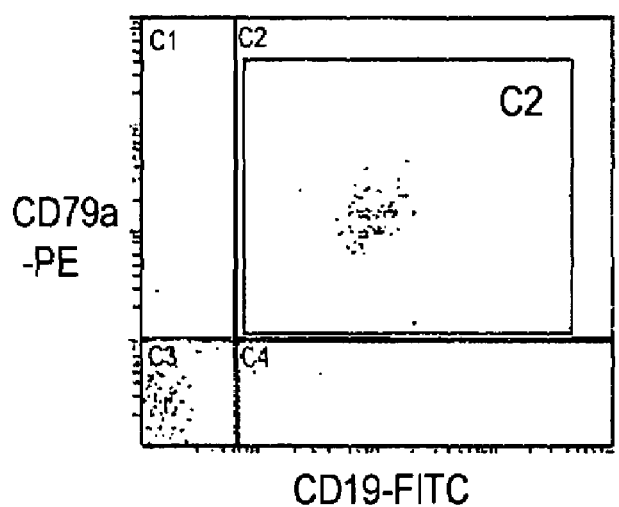
Figure 3B:
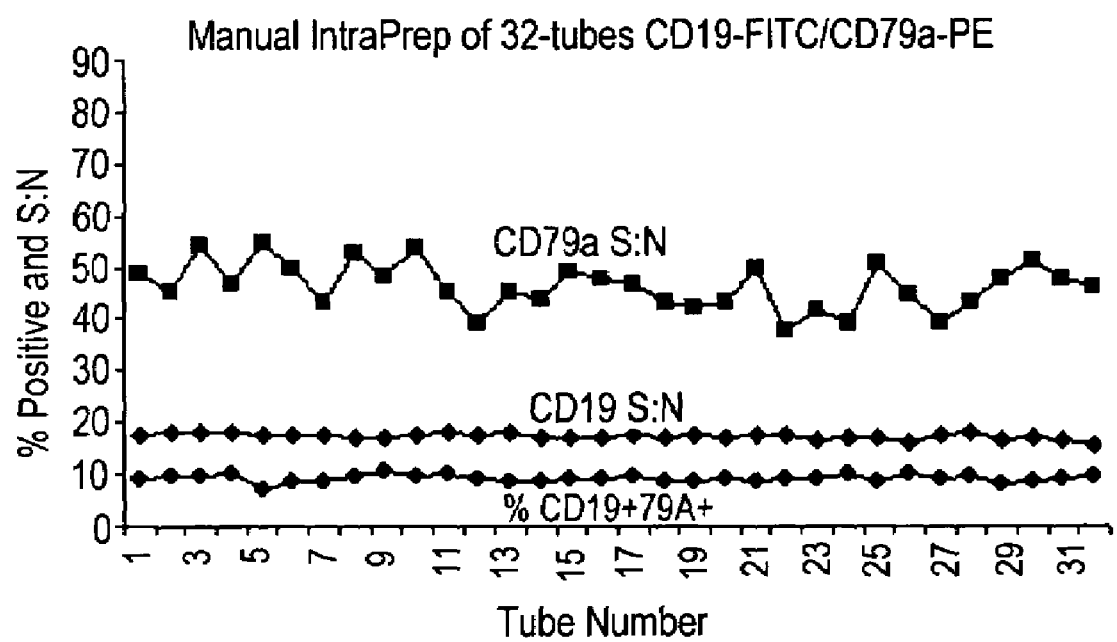

Conventional Method of Preparing Cell Samples for Intracellular Analysis 20 microliters of a cell surface probe were manually pipetted into each of thirty-two different 12×75 test tubes. The cell surface probe comprised a fluorochrome-labeled monoclonal antibody (CD19 conjugated with a fluorescein isothiocynate (FITC) dye). This antibody is specific to the CD19 surface antigen present on human B-cell lymphocytes. (Unless otherwise stated, the cell surface probe, like all reagents used in the EXAMPLES hereof, is manufactured by Beckman Coulter, Inc., and all reagents are used in accordance with the package insert instructions). A 50 microliter sample of K3 EDTA whole blood (i.e., whole blood containing tri-potassium ethylenediamine tetraacetic acid—an anti-coagulant) obtained by venipuncture from a human subject was then manually pipetted into each of the test tubes, and the contents of each tube were mixed by a gentle swirling of the tube. The tube contents were then incubated at room temperature for 15 minutes and protected from the light, and 100 microliters of paraformaldehyde (PFA) at a concentration of 5.5%, were pipetted quickly into each tube. After swirling the tubes to mix the contents thereof, the tube contents were incubated for 15 minutes at room temperature protected from the light. Thereafter, four milliliters of a phosphate-buffered saline solution (PBS) were added quickly to each tube with sufficient force to mix contents. Each tube was then manually transported to a centrifuge where the respective contents of each tube were then centrifuged for 5 minutes on a Beckman Coulter Model J6B operating at 300×g force. Following such centrifugation, the tubes were removed from the centrifuge and the majority of the resulting supernatant was aspirated from each tube. The tubes were then placed on a vortex mixer (Scientific Industries Vortex Genie Touch Mixer) and the small volume of remaining supernatant and the pellet of cells resulting from the centrifugation were subjected to a brief period of vortex mixing sufficient to resuspend the cells in the supernatant (buffer). Thereafter, one hundred microliters of a saponin solution, a permeabilizing/lysing reagent, with a concentration of 0.7% were added to each tube and incubated at room temperature protected from the light for 5 minutes. Thereafter, twenty microliters of an intracellular probe were pipetted quickly into each tube. The intracellular probe, made and sold by Beckman Coulter and used in accordance with the package insert instructions, was a fluorochrome-labeled monoclonal antibody CD79a conjugated with a phycoerythrin (PE) dye. This intracellular probe was added to each tube to label the intracellular molecules of interest (i.e., the CD79a intracellular antigen of the B-cell antigen receptor complex—an antigen important in the diagnosis of leukemia). Following a 15 minute incubation period at room temperature protected from the light, four milliliters of phosphate-buffered saline (PBS) were added quickly to each tube with sufficient force to mix the contents, and the respective contents of each tube were again subjected to centrifugation for 5 minutes using a 300×g centrifugation force. After aspirating the majority of the supernatant, one milliliter of PBS containing 0.5% paraformaldehyde was pipetted into each tube. Upon vortex mixing the sample in each tube for a time sufficient to re-suspend the pelleted cells, each tube and the prepared cell sample therein was presented to a Beckman Coulter EPICS® XL/MCL™ 4-color Flow Cytometer utilizing EXPO-ADC software (available from Beckman Coulter, Inc.) for data acquisition and analysis. In this analysis, forward and side scattered light were used to gate the lymphocyte population of white blood cells and, of this population, the CD19 and CD79a-positive were detected (see the scattergram of FIG. 3A, region C2). As shown in FIG. 3B, the percentage of such cells in each of the thirty-two prepared samples ranged between about 8 and 10%. Also shown in FIG. 3B are the respective signal-to-noise ratios (S:N) of each of the parameters of the dual CD19 and CD79a-positive cells. The signal-to-noise ratio is calculated by dividing the mean fluorescence intensity (MFI) of the positive population (e.g. the y-axis mean of the population in region C2 of FIG. 3A), by the MFI of the negative population (e.g. the y-axis mean of the population in region C3 of FIG. 3A). As is apparent, the S:N of he CD-19-positive cells is relatively constant, whereas the S:N of the CD79a intracellular marker varies considerably from sample to sample.

EXAMPLE 2

Figure 4A:
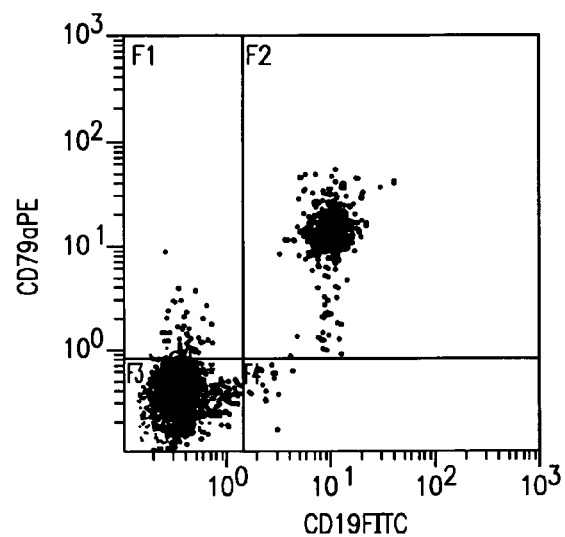
Figure 4B:
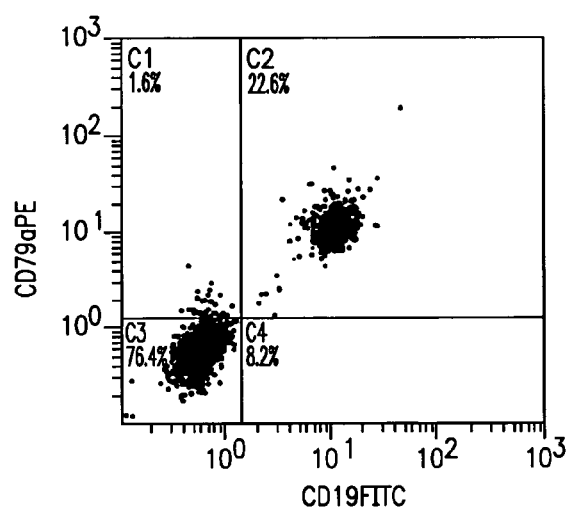
Figure 4C:
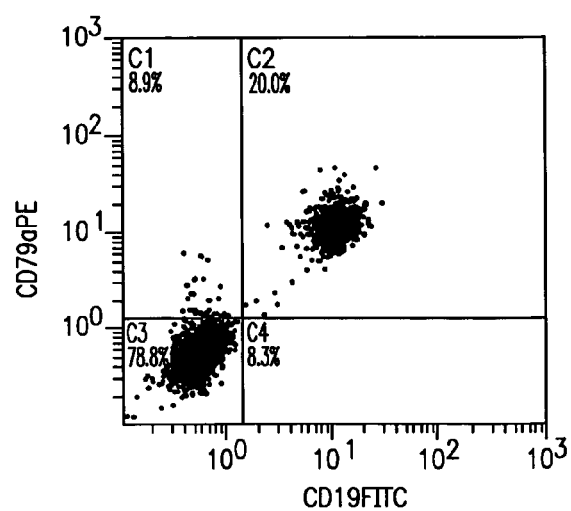

New Method for Preparing a Whole Blood Sample for Detection of Intracellular CD79a Antigen in B-cell Lymphocytes As in Example 1 above, 20 microliters of a fluorochrome-labeled antibody (CD19-FITC) were manually pipetted into each of six different 12×75 mm test tubes arranged in a carousel-type tube holder. As noted above, the antibody is a monoclonal antibody specific to the CD19 surface antigens carried by B-cell lymphocytes. A 50 microliter sample of K3 EDTA whole blood obtained by venipuncture from a human subject was then manually pipetted into each of the test tubes and the contents of each tube were mixed by a gentle rocking of the tube. The tube contents were then incubated at room temperature for 15 minutes. Thereafter, 25 microliters of paraformaldehyde (PFA) at a concentration of 5.5%, were pipetted into each tube. After gently rocking the tubes to mix the contents thereof, the tube contents were incubated for 20 minutes. Then, 20 microliters of the intracellular probe (CD79a conjugated with a phycoerythrin (PE) dye) was added to four of the six tubes, immediately followed by the addition of 100 microliters of saponin having a concentration of 0.7%. After a gentle mixing of the tube contents, each tube was incubated for 45 minutes. Into the remaining two tubes, 20 microliters of the intracellular probe, Isotype-PE were pipetted. This second probe is used to gate-out negative cells in the flow cytometer analysis to follow. Thereafter, 600 microliters of a phosphate-buffered saline solution (PBS) were added to each tube. Three of the six tubes, one containing the Isotype probe and two containing the CD79a probes, were then presented to a Beckman J6B centrifuge for centrifugation for 5 minutes at 300 g force. Following centrifugation, the resulting supernatant was aspirated and 1 milliliter of PBS/PFA was added. These three tubes were then subjected to vortex mixing to resuspend the sample and thereby ready it for analysis. The remaining three tubes were presented to the CellPrep cell-washing instrument, where the processed cell samples were automatically filtered (i.e. washed) in accordance with Protocol 2, a particular cell-washing protocol programmed into the instrument. According to this protocol, the tube contents are first aspirated from each tube and drawn into the hollow fiber that serves to filter the cell sample. As noted earlier herein, such hollow fiber comprises a cylindrical wall made of a semi-permeable membrane that serves as a filter for removing relatively small (compared to the cells of interest) interferant particles from the cell sample. Such filtering is effected by applying a vacuum force to the fiber exterior, whereby the relatively small interferant particles pass through the fiber's semi-permeable membrane and then to waste. Meanwhile, the cells of interest remain within the fiber. According to Protocol 2, this filtering action is performed twice, i.e., the once-filtered particles are then re-suspended within the fiber by adding a buffer solution to the fiber and then applying the vacuum force for a second time. Thereafter, the cells of interest are flushed out of the fiber by pumping 1 milliliter of an isotonic buffer solution through the fiber. The twice-filtered cells are returned to their original container (test tube) where they are re-suspended in the flushing solution. Each of the six tubes was then presented to a Beckman Coulter Cytomics FC500™ flow cytometer utilizing RXP software (available from Beckman Coulter) for data acquisition and analysis. The results of this analysis are shown in FIGS. 4A and 4B. In FIG. 4A, the cell sample was washed by the centrifugation process described above; in FIG. 4B, the cell sample was washed by the hollow fiber filtering scheme described. Using the same blood sample and reagents, the conventional manual method described in EXAMPLE 1 was used to prepare the sample for intracellular analysis. The same flow cytometer was used to analyze the sample, and the results of this analysis are shown in FIG. 4C. As will be appreciated from the scattergrams of FIGS. 4A-4C, the three manually-performed methods for sample preparation, two being new and in accordance with the invention illustrated in FIG. 2A, and one being in accordance with the conventional method illustrated in FIG. 1, provide very comparable results.

EXAMPLE 3

Semi-Automation of the Sample Preparation Method of the Invention

Figure 5:
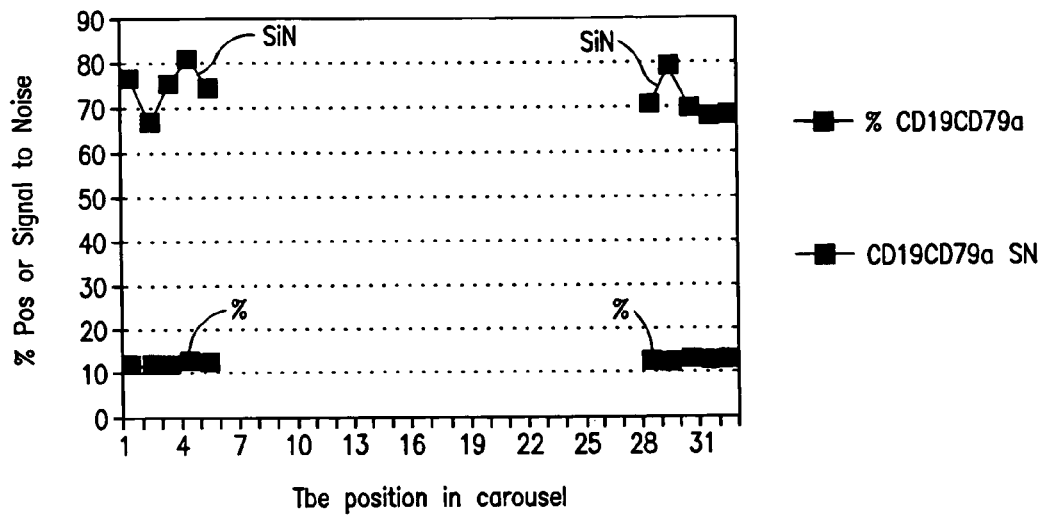

In this Example, the sample preparation method depicted in FIG. 2A is carried out "semi-automatically" in that although all of the method steps are performed by two automated instruments, there is a manual step of transporting a carousel of samples, totally prepared except for the final wash step, from one instrument to the other. To begin, a 75 mm tube of whole blood collected in a K3 EDTA Vacutainer tube from a human donor was placed in the specimen cassette of the Beckman Coulter PrepPlus2 pipetting/incubating instrument. This instrument comprises a programmable mechanism that controls the XYZ position of an aspirating/dispensing probe that, for example, dips into a reagent or sample container to aspirate a predetermined volume of liquid therein, and then moves to a test tube in which a cell sample is to be prepared and dispenses a predetermined volume of the aspirated liquid therein. The instrument includes a wash station at which the aspirating/dispensing probe is washed as desired, e.g., between successive aspirations. A reagent rack containing bottles with open (or pierceable) tops of all reagents necessary to carry out the sample preparation method of the invention was suitably placed within the PrepPlus instrument. These reagents included the cell surface probe CD19FITC, the intracellular probe CD79aPE, a paraformaldehyde (PFA) fixative, the permeabilizing/lysing reagent, a 0.7% solution of saponin, and different isotonic buffer solutions. A thirty-two tube carousel-type holder containing 10 empty 12×75 polypropylene tubes were placed on the instrument. The 10 empty tubes were placed in carousel positions 1-5, and 28-32 to verify that the results are not carousel position-dependent. The microprocessor of the PrepPlus2 instrument was programmed to cause the instrument to carry out the following steps: first, 20 microliters (the manufacturer's recommended dose) of the cell surface probe (CD19FITC) were pipetted into each of the ten test tubes. Next, the instrument pipetted into each of the test tubes a fifty microliter sample of K3 EDTA whole blood obtained by venipuncture from a human subject. The pipetting force of the entering blood served to mix the blood with the cell surface probe. The tube contents were then incubated in the instrument at room temperature for 15 minutes. Next, 25 microliters of the formaldehyde solution were pipetted into each tube in turn and incubated at room temperature for 20 minutes. Then, 20 microliters of the intracellular probe (CD79aPE) were added to each tube immediately followed by the addition of 100 microliters of the saponin solution. The ten tubes were then incubated at room temperature for 45 minutes. Thereafter, 600 microliters of IsoFlow™ were added to each tube. The tube-containing carousel was then manually presented to a Beckman Coulter CellPrep instrument which automatically operated on each tube in accordance with its pre-programmed Protocol 2 (described above). Having performed this cell-washing process on all ten tubes, each tube was presented to an Epics XL-MCL Flow Cytometer utilizing Beckman Coulter's System II software for data acquisition and analysis. The results are shown in FIG. 5. In this analysis, forward and side scattered light were used to gate the lymphocyte population of white blood cells and, of this population, the CD19 and CD79a-positive were detected. As shown in FIG. 5, the percentage of such cells in each sample was relatively constant at a level of about 11% across the ten replicate tubes. Also shown in FIG. 5 is the signal-to-noise ratio (S:N) of the CD79a-positive cells.

EXAMPLE 4

Figure 6A:
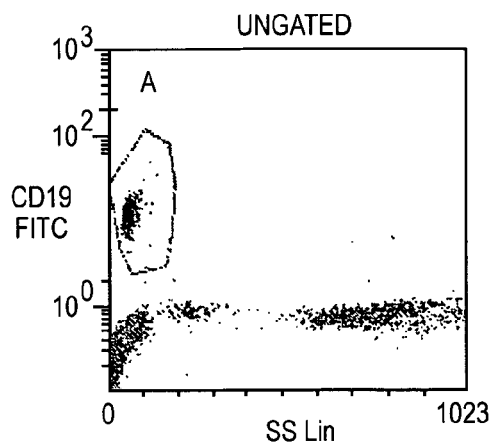
Figure 6B:
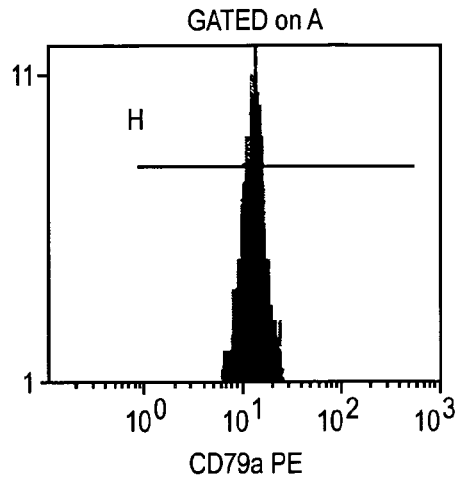
Figure 6C:
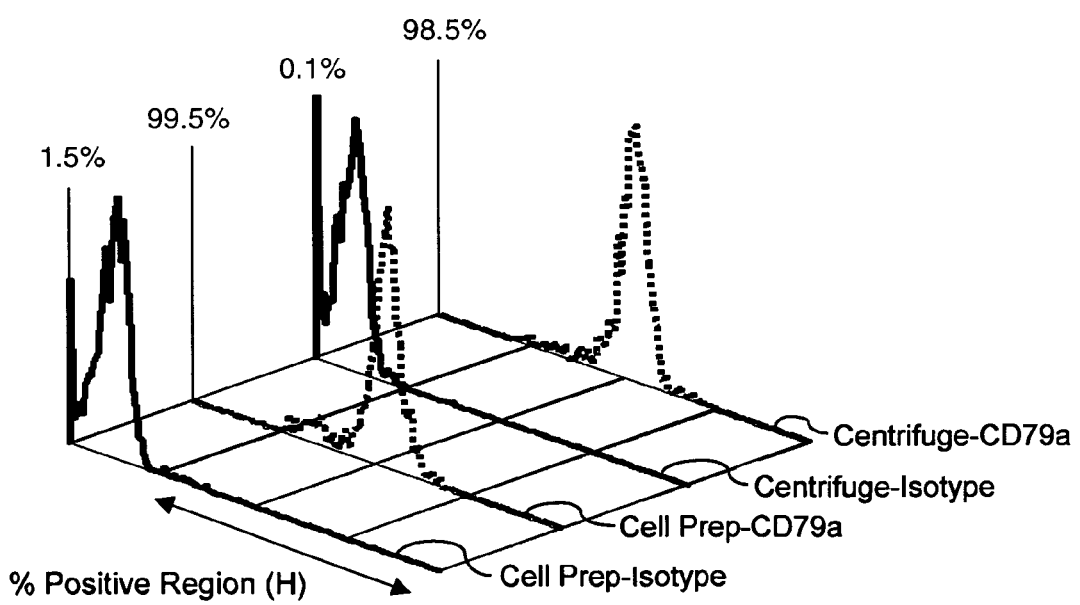

New Methods of Sample Preparation Comparing Hollow Fiber Filtering and Centrifugation Washing Steps In this Example, the cell surface staining was performed off-line (manually); but the steps of fixing, permeabilizing and intracellular (IC) staining was performed automatically in the Beckman Coulter PrepPlus2 instrument. The manufacturer's recommended dose (20 microliters per test) of a fluorochrome-labeled antibody (CD19 conjugated with a fluorescein isothiocynate (FITC) dye) was manually pipetted into each of six different 12×75 mm test tubes. The antibody was a monoclonal antibody specific to the CD19 surface antigens present on B cells. A fifty microliter sample of EDTA whole blood obtained by venipuncture from a human subject was then manually pipetted into each of the test tubes and the contents of each tube were mixed by a gentle swirling of the tube. The tube contents were then incubated at room temperature for 15 minutes protected from the light. The six tubes were then placed in a carousel-type tube holder, which was then placed onto a PrepPlus2 instrument that performed the pipetting and incubation steps (according to a modified software protocol) as described next. Twenty-five microliters of paraformaldehyde (PFA) at a concentration of 5.5%, were pipetted into each tube and incubated for 20 minutes. Then, 20 microliters of isotype-PE was pipetted into two tubes and 20 microliters of CD79a-PE was pipetted into the remaining 4 tubes. (The isotype probe is used, but not always shown, to detect non-specific protein-binding and is used to determined the lower threshold of a positive analysis region. Each antibody addition was followed by the addition of 100 microliters of saponin, at a concentration of 0.7% to all six tubes. The tubes were incubated on the PrepPlus2 until the addition of 600 microliters of IsoFlow™, an isotonic solution made by Beckman Coulter. Three tubes (one containing a calibrating Isotype probe and two containing the intracellular CD79a probe) were removed from the carousel and placed in a Beckman J6B centrifuge for 5 minutes at 500×g force. The majority of the supernatant was aspirated and 1 ml of IsoFlow was added. The tubes were swirled to resuspend the cells. The three remaining tubes on the carousel were transported to a CellPrep cell washing instrument, where each tube in turn was filtered according to Protocol 2. Each of the six tubes was then presented in turn to a Beckman Coulter Cytomics FC500 flow cytometer utilizing the RXP software (noted in EXAMPLE 2) for data acquisition and analysis. Results of such analysis are summarized in FIGS. 6A-6C. The Overlay Plot of FIG. 6C is comprised of four histograms from four different sample-preparations similar to that shown in FIG. 6B which shows the CD79a expression in a CD19-positive lymphocyte populations that has been gated as shown in FIG. 6A. "Centrifuge" indicates that the cell samples were prepared as shown in FIG. 2A, except that the single wash step was performed using a traditional centrifuge. "Cell-Prep" indicates that samples were prepared as shown in FIG. 2A and filtered using the hollow fiber technology used in the CellPrep instrument. "Isotype" indicates the samples were stained with CD19-FITC and Isotype-PE. "CD79a" indicates the samples were stained with CD19-FITC and CD79a-PE. Conclusion: the hollow fiber wash method performed here is comparable to the conventional centrifugal method of cell washing in the detection of intracellular CD79a inside CD19 B cells present in EDTA whole blood preparations.

EXAMPLE 5

Figure 7A:
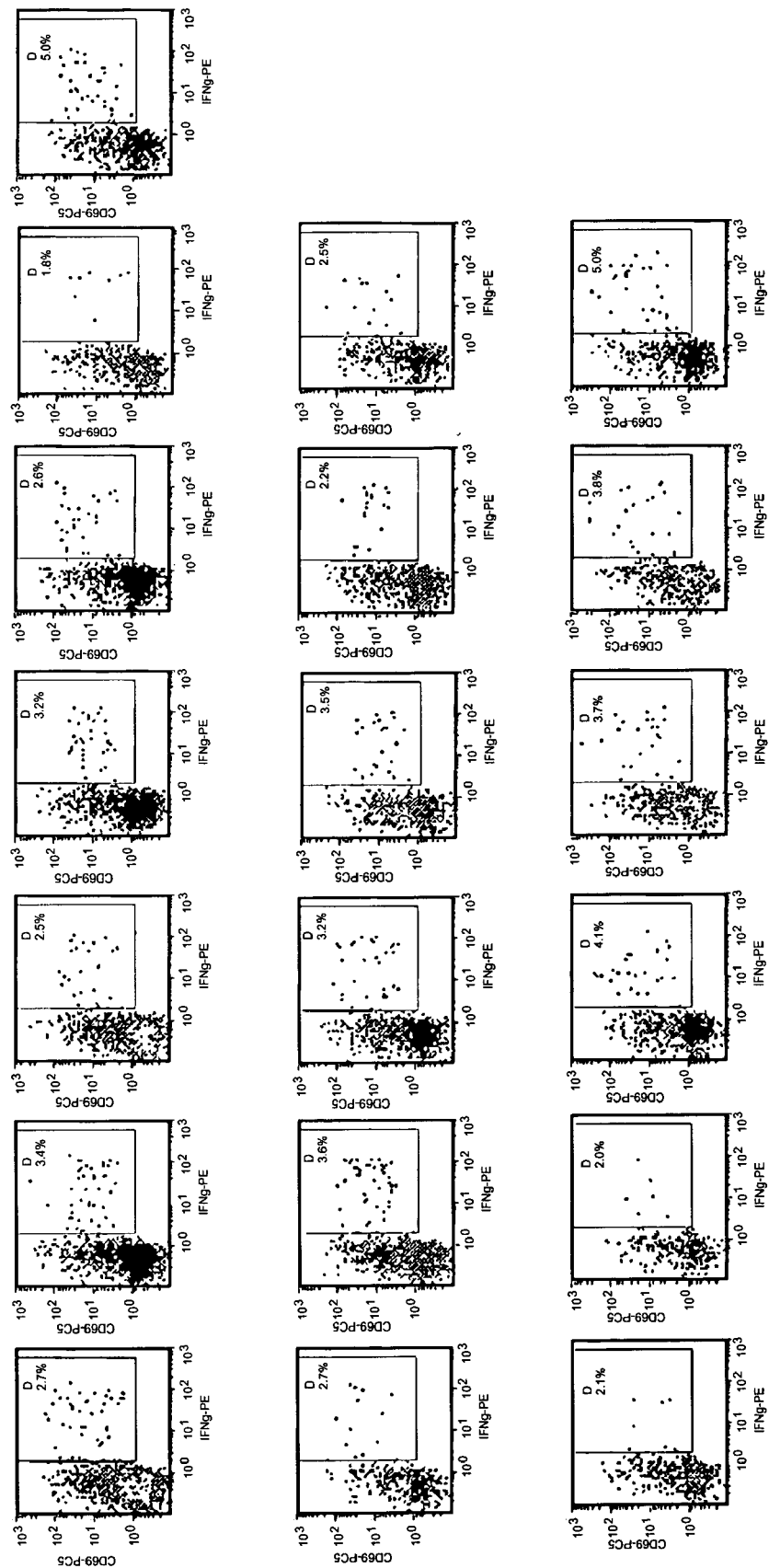

Repeatability of Semi-Automated Sample Preparation Method of the Invention vis-a-vis the Conventional Manual Method Heparinized whole blood was obtained by venipuncture of a human subject and five hundred microliters of such blood was pipetted into each of nine standard fifteen milliliter culture tubes with (stimulated) traditional lymphocyte stimulating agents (SEB and the co-stimulating antibody CD28). The culture tubes were then placed in an incubator set at 35° C. for 90 minutes. Five microliters of Brefeldin-A containing 2.5 micrograms (a dose sufficient to prevent cytokine secretion) was added then to each of the nine cultures. The tubes were replaced in the incubator for an additional 16 hours. After a total of 17.5 hours culture time, the nine cultures were pooled into a single culture tube and mixed gently. Nineteen cell samples were prepared for intracellular analysis according to the conventional method described in EXAMPLE 1 with the surface probes being the manufacturer's recommended doses of two fluorochrome-labeled antibodies, one antibody being CD4 conjugated with a fluorescein isothiocyanate (FITC) dye, specific to the CD4 antigen present on the surface of T-helper lymphocytes; and the other antibody being CD69 conjugated to phycoerythrin-cyanine 5 tandem dye (PC5), specific to the CD69 surface antigen present on most activated lymphocytes. The intracellular probe used was the manufacturer's recommended dose of twenty microliters of the specific intracellular cytokine probe interferon-gamma (IFNg) conjugated with a phycoerythrin (PE) dye. The specimen was a fifty microliter sample of stimulated cultured blood added to each tube. The wash buffer was a PBS solution containing 0.1% sodium azide. After the final centrifugation and vortex mixing steps, each of the nineteen tubes was presented to a Beckman Coulter Cytomics FC500 flow cytometer utilizing the RXP software, noted in EXAMPLE 2, for data acquisition and analysis. The results of these analyses are shown in FIG. 7A.

Figure 7B:
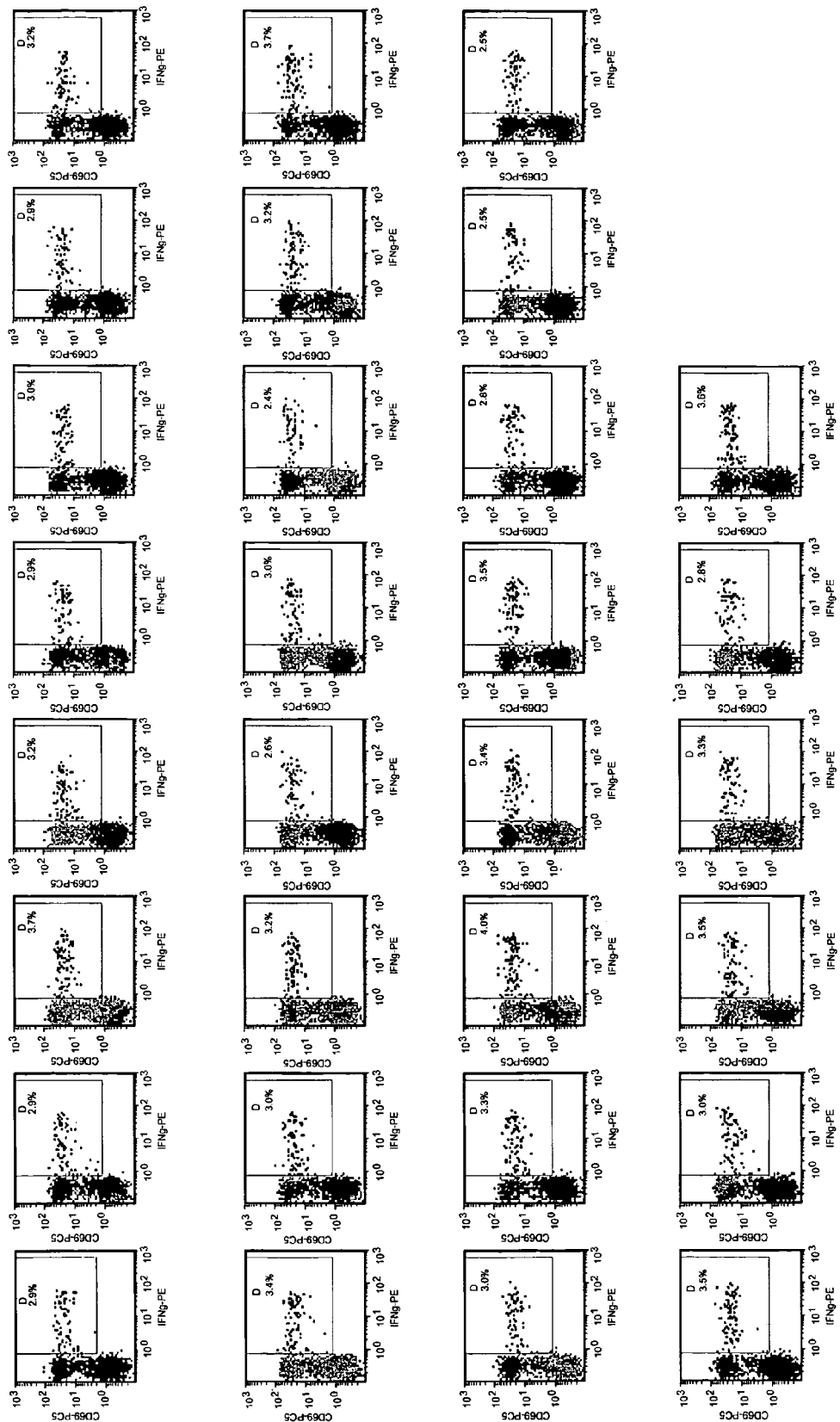

Thirty other cell samples were prepared for intracellular analysis using the method illustrated in FIG. 2A. More specifically, 2.5 milliliters of stimulated blood was placed into a 75 mm tube having a pierceable cap and this specimen was placed onto the PrepPlus2 pipetting instrument. Two probe reagent bottles containing the two probes for surface molecules as described above, and a carousel-type holder containing thirty empty 12×75 staining tubes were placed on the PrepPlus2 instrument. The PrepPlus2 instrument's standard software was modified to direct the following pipetting steps: addition of 10 ul of CD69-PC5 to each tube, addition of 20 ul of CD4-FITC to each tube, and finally addition of 50 ul stimulated whole blood specimen to each tube. The staining samples were left in the carousel on the instrument for 15 minutes at room temperature. The standard reagent rack that normally contains the surface probes normally used in the PrepPlus2 instrument was replaced with a modified reagent rack containing the intracellular probe reagent (described above), a 5.5% paraformaldehyde solution, and a 0.7% saponin solution. The instrument was then directed, by its software, to perform the pipetting and incubation steps (according to a modified software protocol) described here: 25 microliters of the paraformaldehyde solution were pipetted into each tube in turn and incubated for 20 minutes. Then 20 microliters of the specific intracellular cytokine probe (IFNg) was added to each tube immediately followed by the addition of 100 microliters of the saponin solution. The tubes were incubated for 45 minutes. Thereafter, 600 microliters of IsoFlow buffer were added to each tube. The carousel was then transported to a CellPrep instrument, where each tube in turn was filtered with the standard IsoFlow reagent according to the standard Protocol 2 shipped with the instrument. Each of the thirty tubes was then presented to a Beckman Coulter Cytomics FC500 flow cytometer utilizing the above-noted RXP software for data acquisition and analysis. The results of such analyses are shown in FIG. 7B. In each of the two-dimensional scattergrams shown in FIGS. 7A and 7B, CD4-positive lymphocytes are plotted with the X-axis representing the IFNg-PE fluorescence intensity, and the Y-axis representing the CD69-PC5 fluorescence intensity. The CD4+CD69+IFNg+ triple-positive population of interest is shown in the upper right-hand quadrant in each scattergram. It will be appreciated that there is a relatively high degree of variability in this quadrant in the nineteen samples produced by the manual method of the prior art (FIG. 7A), whereas, in the thirty scattergrams shown in FIG. 7B, there is a remarkable degree of consistency in the location of the triple-positive cells shown in this quadrant. The coefficient of variation (CV) was calculated from the average values recorded from the thirty scattergrams in FIG. 7B, and of the nineteen scattergrams of FIG. 7A; the results are shown in TABLE 1A below. The two values measured were the percentage (%) of lymphocytes that were triple-positive for the three probes used (in the upper right-hand corner), and the mean fluorescence intensity (MFI) of the IFNg-PE probe on the triple-positive lymphocytes shown on each scattergram within the quadrant of interest. The semi-automated method of the invention demonstrates much better precision (almost two-times better) than the conventional method for the simultaneous detection of intracellular cytokine and surface antigens. Factors that contribute to this increased precision of the new method are: the rigid control of the reagent volumes, mixing and incubation times; the reduction in the number of processing steps, and the single, relatively gentle cell-washing step at the end of the sample-preparation method. The accuracy of the new method is compared with that of the conventional manual method in TABLE 1 B below. These values represent the average of the 19 replicates (produced by the conventional method) and the 30 replicates (produced by the new method.)

TABLE 1A

|  | CV Conventional | CV Automated |
|---|---|---|
| % CD4+CD69+IFNg+ triple-positive events | 25.2 | 12.9 |
| MFI of IFNg in CD4+CD69+IFNg+ triple-positive events | 30.3 | 17.4 |

TABLE 1B

|  | Average for Conventional | Average for Automated |
|---|---|---|
| % CD4+69+IFNg+ | 3.10 | 3.31 |

EXAMPLE 6

Detection of IFNg in Stimulated Whole Blood from Samples Prepared by Semi-Automated Method of FIG. 2B and by Conventional Method of FIG. 1

Figure 8A:
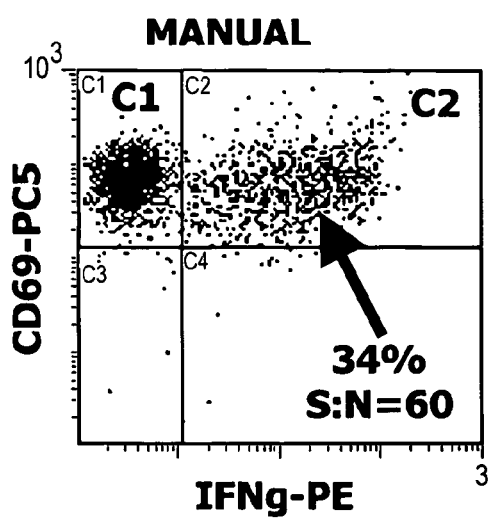
Figure 8B:
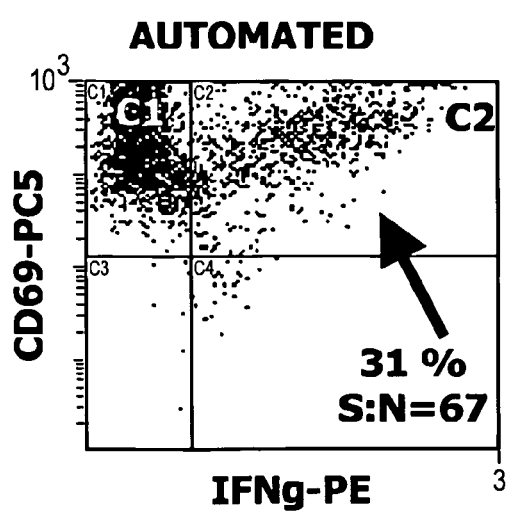

Heparinized whole blood obtained by venipuncture of a human subject was diluted with equal volume of AIM-V serum-free media (Gibco). Five hundred microliters of such blood was pipetted into a standard fifteen milliliter culture tube with the following traditional lymphocyte stimulating agents: 250 micrograms of PMA, and 0.5 micrograms of ionomycin. The culture tube was then placed in an incubator set at 35° C. for 120 minutes. Five microliters of Brefeldin-A containing 2.5 micrograms (a dose sufficient to prevent cytokine secretion) was added then to the culture. The tube was replaced in the incubator for an additional twenty-two hours. A cell sample was prepared for intracellular analysis according to the conventional method described in EXAMPLE 1 with the surface probes being the manufacturer's recommended doses of two fluorochrome-labeled antibodies (10 microliters per test) of antibodies CD3 conjugated with a fluorescein isothiocyanate (FITC) dye, specific to the CD3 antigen present on the surface of T-lymphocytes; and CD69 conjugated to phycoerythrin-cyanine 5 tandem dye (PC5), specific to the surface antigen present on most activated lymphocytes). The intracellular probe used was the manufacturer's recommended dose of twenty microliters of the specific intracellular cytokine probe Interferon-gamma (IFNg) conjugated with a phycoerythrin (PE) dye. The specimen was a fifty microliter sample containing the stimulated cultured blood. The wash buffer was a PBS solution containing 0.1% sodium azide. Another cell sample was prepared for intracellular analysis according to the method shown in FIG. 2B. More specifically, the two probes for surface molecules and the single intracellular molecule probe were pipetted simultaneously into a 12×75 mm tube in a carousel-type tube holder. A fifty microliter sample of the specimen described above was pipetted into the 12×75 mm tube and the tube contents were incubated for fifteen minutes at room temperature protected from the light. The carousel was then manually placed onto a PrepPlus2 instrument that performed the pipetting and incubation steps (according to a modified software protocol) described here. To the tube, in turn, were added one-hundred microliters of a paraformaldehyde (PFA) solution at a concentration of 5.5%, one-hundred microliters of a red blood cell lysing reagent (1× concentration of ammonium chloride solution (10× IOTest3 Lysing Reagent, available from Beckman Coulter)), and one-hundred microliters of a saponin solution at a concentration of 0.7%. The tube was held at room temperature for 20 minutes. Thereafter, 600 microliters of PBS were added to the tube, and the carousel was manually transported to a CellPrep instrument, where the tube was filtered with the standard IsoFlow reagent, according to a standard Protocol 2 embedded in the instrument. Each of the two tubes, one prepared by the conventional method (FIG. 1) and the other prepared by the method of FIG. 2B) was then presented to an EPICS XL-MCL flow cytometer utilizing EXPO-ADC software, for data acquisition and analysis. The results of such analysis are summarized in the scattergrams of FIGS. 8A and 8B, each showing the CD3 + lymphocytes. The signal-to noise ratio (S:N) is calculated by dividing the x-mean of gated region C2 by the x-mean of region C1. The percentage (%) is the percent of cells in region C2, which are CD3+,CD69+, and IFNg+. "Manual" refers to results attained from samples prepared by the conventional method of FIG. 1, and "Automated" refers to results attained from samples prepared by the method of FIG. 2B, as semi-automated by the use of the PrepPlus2 and CellPrep instruments. It will be appreciated that the scattergrams illustrate that the two sample-preparation methods produce comparable results, and that the intracellular cytokine and surface antigens are detectable simultaneously.

EXAMPLE 7

Detecting CD 79a in a Previously Frozen PBMC Cell Sample Comparing Samples Prepared by the Methods Depicted in FIGS. 1 and 2A Peripheral Blood Mononuclear Cells (PBMC) were prepared, frozen, and thawed according to methods known to those skilled in the art. As in EXAMPLE 1, the manufacturer's recommended dose (20 microliters per test) of a fluorochrome-labeled antibody (CD19 conjugated with a fluorescein isothiocynate (FITC) dye) was manually pipetted into each of eight different 12×75 mm test tubes arranged in a carousel-type tube holder. The antibody was a monoclonal antibody specific to the CD19 surface antigens present on B-cell lymphocytes. A fifty microliter sample containing 500,000 thawed human PBMC cells was then manually pipetted into each of the test tubes and the contents of each tube were mixed by a gentle swirling of the tube. The tube contents were then incubated at room temperature for 15 minutes protected from the light. Four of the tubes were then prepared manually according to the conventional method described in EXAMPLE 1 and using the reagents noted below. The remaining four tubes were placed in a carousel-type tube holder, which was then placed onto a PrepPlus2 instrument that performed steps (b) through (e) of the method illustrated in FIG. 2A. The fixative was 25 microliters of paraformaldehyde (PFA) at a concentration of 5.5%; the intracellular probe was either (a) 20 microliters of CD79a conjugated with a phycoerythrin (PE) dye (in two tubes), or (b) 20 microliters of the isotype probe conjugated with a phycoerythrin (PE) dye (in two tubes); and the permeabilizing reagent was 100 microliters of saponin at a concentration of 0.7%. The incubation times following fixation and permeabilization were 20 and 45 minutes, respectively, both being at room temperature. After permeabilization and the subsequent incubation period, 600 microliters of IsoFlow buffer were added to each of the four tubes. The carousel containing the four tubes was then manually transported to a CellPrep instrument, where each tube in turn was filtered according to Protocol 2. Each tube was then presented to a Beckman Coulter Cytomics FC500 flow cytometer utilizing RXP software, for data acquisition and analysis. The results of such analysis are summarized in FIGS. 9A-9D. As shown in FIG. 9A, the gating scheme uses the forward scatter (FS) and side scatter (SS) measurements to isolate the lymphocyte population A of cells in the analyzed sample. Of these lymphocytes, those positive for CD19 (region B of FIG. 9B) were interrogated for CD79a expression FIG. 9C. The overlay plot of FIG. 9D compares four different samples gated as described in FIGS. 9A-9C (e.g., CD79a expression in CD19 positive lymphocyte populations, as shown in FIG. 9C.) "Manual" indicates that samples were prepared as in EXAMPLE 1 (Conventional Method). "Automated" indicates that samples were prepared as described in this example. "Isotype" indicates the samples were stained with CD19-FITC and Isotype-PE. "CD79a" indicates the samples were stained with CD19-FITC and CD79a-PE. Conclusion: the automated method described here is comparable to the conventional method of the prior art in detection of intracellular CD79a inside CD19, B cells, present in frozen and thawed PBMC preparations.

EXAMPLE 8

Detection of TNFa in Stimulated Fresh PBMCs Comparing Samples Prepared by the Methods Depicted in FIGS. 1 and 2A Fresh Peripheral Blood Mononuclear Cells (PBMC) were prepared from heparinized whole blood obtained by venipuncture from two different human donors according to methods known to those skilled in the art. Five million PBMC of each donor in 0.5 milliliter of traditional RPMI culture medium supplemented with 10% Human AB Serum, were then placed into a standard fifteen milliliter culture tube with (stimulated) traditional lymphocyte stimulating agents (Staphylococcus Enterotoxin B, SEB, and co-stimulant anti-CD28 antibody). This was repeated with 2.5 million PBMC of each donor in 0.5 milliliter culture medium. The two culture tubes were placed in a LabPack incubator, set at 37° C. and supplemented with 5% $CO_2$, for 90 minutes. Five microliters of Brefeldin-A containing 2.5 micrograms (a dose sufficient to prevent cytokine secretion) was added then to each of the culture tubes. The tubes were then incubated for an additional 16 hours.

Two fifty microliter samples of each of the two culture tubes were prepared as duplicates according to the conventional method illustrated in EXAMPLE 1 with the surface probes being the manufacturer's recommended doses (10 microliters per test) of the following four fluorochrome-labeled antibodies: CD8 conjugated with a fluorescein isothiocyanate (FITC) dye, specific to the CD8 antigen present on the surface of T-cytotoxic lymphocytes; CD69 conjugated to phycoerythrin-cyanine 5 tandem dye (PC5), specific to the surface antigen present on most activated lymphocytes); CD4 conjugated with a phycoerythrin-Texas red (ECD) tandem dye, specific to the CD4 antigen present on the surface of T-helper lymphocytes; and CD3 conjugated to phycoerythrin-cyanine 7 (PC7) tandem dye, specific for the CD3 antigen present on all T lymphocytes). The intracellular probe used was the manufacturer's recommended dose of twenty microliters of the specific intracellular cytokine probe tumor necrosis factor-alpha (TNFa) conjugated with a phycoerythrin (PE) dye. The fixative was paraformaldehyde (PFA) at a concentration of 5.5%, and the permeabilizing reagent was saponin at a concentration of 0.7%.

The wash buffer was a PBS solution containing 0.1% sodium azide and 2% fetal calf serum (FCS).

Four other samples were prepared as duplicates, two samples being from each of the two culture tubes using the method of FIG. 2A; the method was semi-automated by the use of the above-described PrepPlus2 and CellPrep instruments. All reagents as used in the conventional sample preparation method described above were the same. Upon completion of the sample preparation methods, the eight tubes were presented to a Beckman Coulter Cytomics FC500 flow cytometer utilizing RXP software, for data acquisition and analysis. The results summarized in TABLE 2 below represents the averaged value from the two tubes prepared from each of the two cultures. As shown in the table, the respective percentages of quadruple-positive lymphocytes (determined by the gating scheme shown in FIG. 16A) for two different combinations of probes (i.e., CD3+CD8+CD69+TNFa+, and CD3+CD4+CD69+TNFa+) found in the PBMC samples from two different concentrations (5 million and 2.5 million PBMC) from the two donors have been recorded. It is apparent that the sample preparation method of the invention yields substantially the same values as the conventional manual method for fresh cultured PBMCs.

TABLE 2

|  | Donor 1 | | Donor 2 | |
| --- | --- | --- | --- | --- |
|  | PRIOR ART METHOD | NEW METHOD | PRIOR ART METHOD | NEW METHOD |
| 5 Million PBMC Conc. | | | | |
| % CD3+CD8+CD69+TNFa+ | 5.38 | 4.69 | 5.32 | 5.29 |
| % CD3+CD4+CD69+TNFa+ | 2.47 | 2.5 | 4.71 | 5.12 |
| 2.5 Million PBMC Conc. | | | | |
| % CD3+CD8+CD69+TNFa+ | 5.13 | 5.23 | 8.65 | 8.29 |
| % CD3+CD4+CD69+TNFa+ | 4.82 | 4.96 | 8.98 | 9.11 |

EXAMPLE 9

Detecting Intracellular Vimentin and Tubulin either Alone or Simultaneously in a Previously Frozen PBMC Cell Sample from Samples Prepared by Methods Depicted in FIGS. 1 and 2A Peripheral Blood Mononuclear Cells (PBMC) were prepared, frozen, and thawed according to methods known to those skilled in the art. The manufacturer's recommended doses (10 microliters per test) of three different probes specific to certain antigens on the surface of various lymphocytes in a blood sample were manually pipetted into each of twelve different 12×75 mm test tube. The three cell-surface probes used were the following fluorochrome-labeled monoclonal antibodies: CD3 conjugated with a phycoerythrin (PE) dye specific to the CD3 antigen present on the surface of T-lymphocytes; CD4 conjugated with a phycoerythrin-Texas red energy coupled dye (ECD) specific to the CD4 antigen present mainly on the surface of T-helper lymphocytes; and CD8-conjugated with a phycoerythrin cyanine-5 tandem dye (PC5) specific to the CD8 antigen present mainly on the surface of T-cytotoxic lymphocytes). A fifty microliter sample containing between about 250,000-500,000 thawed human PBMC cells was then manually pipetted into each of the test tubes and the contents of each tube were mixed by a gentle swirling of the tube. The tube contents were then incubated at room temperature for 15 minutes protected from the light. Six of the tubes were then prepared according to the method described in EXAMPLE 1 and using two intracellular antigen probes either alone or simultaneously. Two tubes received one intracellular probe, two tubes received the other intracellular probe, and two tubes received both probes. The two intracellular probes used were: anti-Vimentin conjugated with a fluorescein isothyocyanate (FITC) dye; and anti-Tubulin conjugated with a phycoerythrin-cyanine-7 (PC7) tandem dye. Vimentin is a variety of intermediate filaments found beneath the nuclear membrane and transversing the cell to give it strength. It is used in oncology research to identify neoplasms. Tubulin protein subunits comprise intracellular molecules that allow cellular movement and provide the "tracks" to transport materials within living cells. Mutation in tubulin are complicated in some therapeutic treatments for Acute Lymphocytic Leukemia (ALL). The remaining six tubes containing the surface probes and the thawed PBMC cells were placed in a carousel-type tube holder and prepared according to method described in Example 3 and depicted in FIG. 2A. The intracellular probes were the same as described above, and each pair of tubes received one or the other or both of the intracellular probes. The fixative (PFA), permeabilizing reagent (saponin) and the incubation periods were as described in EXAMPLES 1 and 2. Each tube was then presented to a Beckman Coulter Cytomics FC500flow cytometer utilizing RXP software, for data acquisition and analysis. The results of such analysis are summarized in FIGS. 10A-10G.

Figures 10A, 10B, 10C:
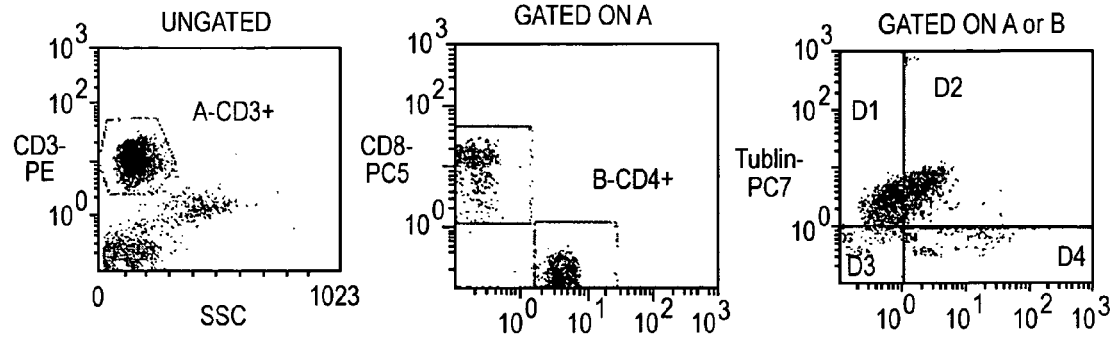
Figure 10D:
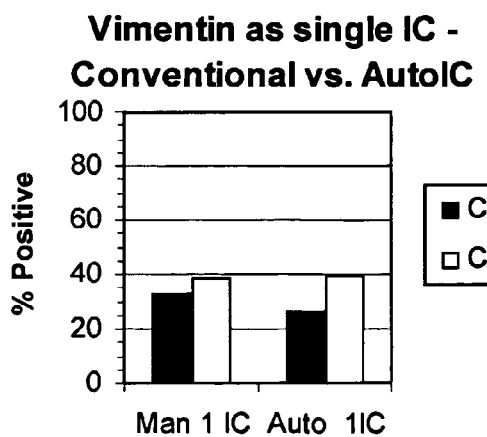
Figure 10E:
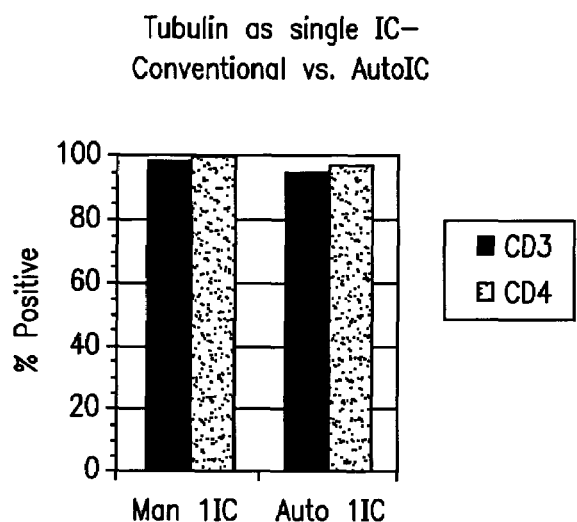
Figure 10F:
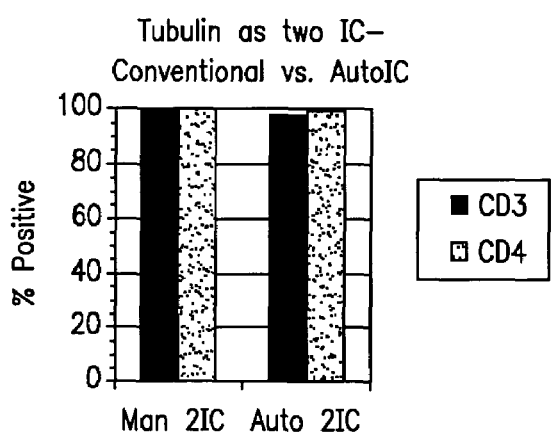
Figure 10G:
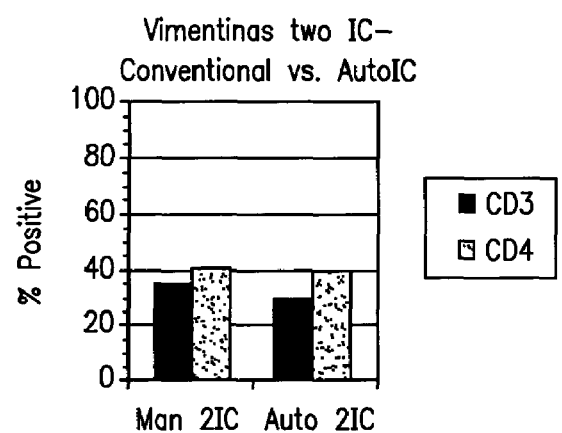
Figure 11A:
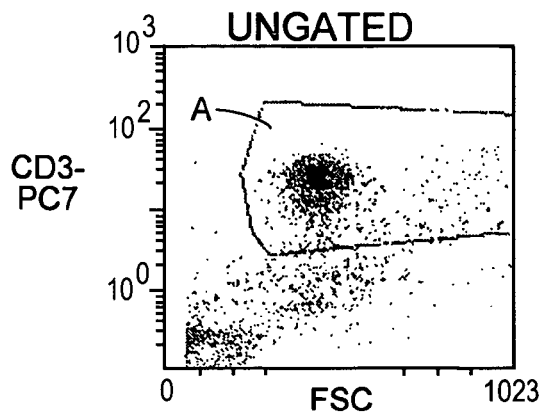
Figure 11B:
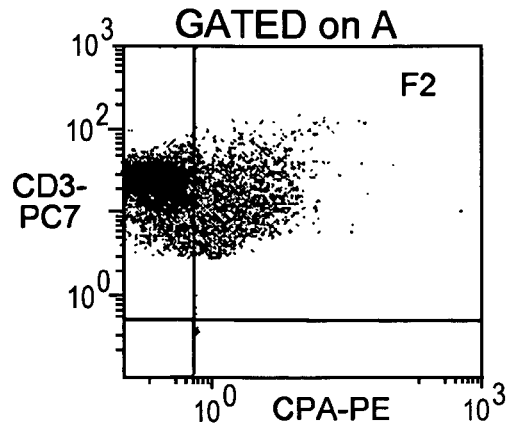
Figure 11C:
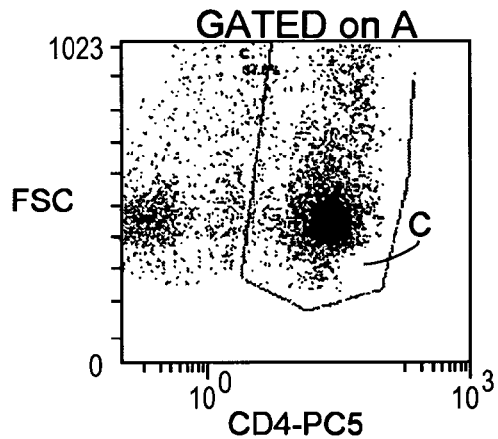
Figure 11D:
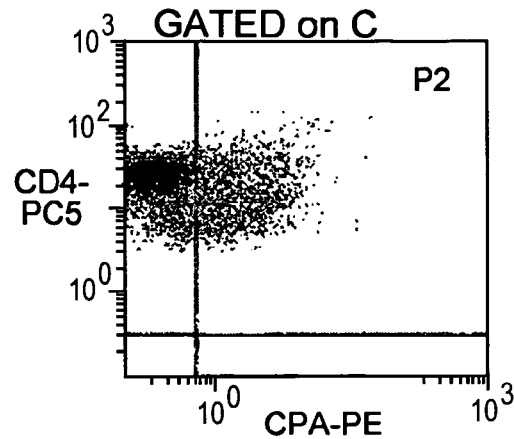
Figure 11E:
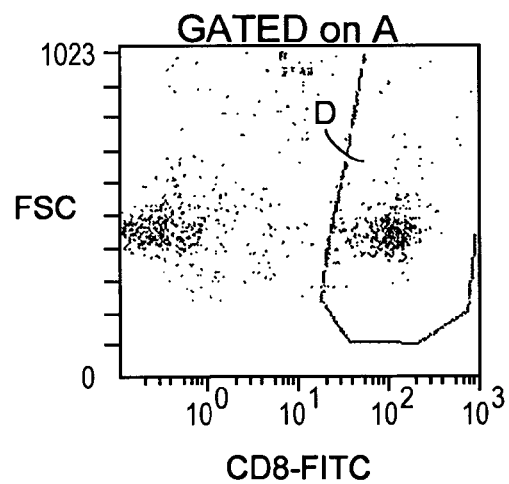
Figure 11F:
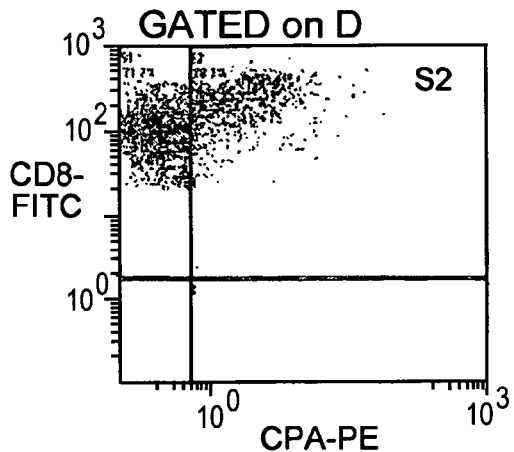

The gating scheme used to determine the values (%) of vimentin- and/or tubulin-positive cells is illustrated in FIGS. 10A-10C. In FIG. 10A, the side-scatter parameter (SSC) is plotted against the CD3 parameter to isolate and gate the CD3-positive lymphocytes (in region A). In FIG. 10B, the CD8 and CD4 parameters are plotted against each other to identify those CD3-positive cells that are also positive for the CD4 surface marker (region B). In the representative scattergram of FIG. 10C, the tubulin and vimentin parameters are plotted against each other to identify those cells that have tested positive for either CD3 (region A) or the combination of CD3 and CD4 (region B). Of the gated cells (regions A or B), those cells that tested positive for both intracellular probes (tubulin and vimentin) are shown in region D2; similarly, of the gated cells, those cells that tested positive for tubulin are shown in regions D1 and D2, and those cells that tested positive for vimentin are shown in regions D2 and D4. The bar graphs of FIGS. 10D-10G compare the test results of those samples prepared by the manual prior art method ("Man") with the test results of those samples prepared by the semi-automated method of the invention ("AUTO"). The values (%) shown in these graphs are the average of duplicate samples. FIG. 10D shows the percentages of vimentin-positive cells that were detected in regions D2 and D4 of those samples that received only anti-vimentin as the IC probe. These vimentin-positive cells were gated from either regions A (CD3-positive) or B (CD3 and CD4-positive). FIG. 10E shows the percentages of tubulin-positive cells that were detected in regions D1 and D2 of those samples that received only anti-tubulin as the IC probe. These tubulin-positive cells were also gated from either regions A (CD3-positive) or B (CD3 and CD4-positive). FIG. 10F shows the percentages of tubulin-positive cells that were detected in regions D1 and D2 of those samples that received both anti-vimentin and anti-tubulin as the IC probes. These tubulin-positive cells were again gated from either regions A or B in FIGS. 10A and 10B. FIG. 10G shows the percentages of vimentin-positive cells that were detected in regions D2 and D4 of those samples that received both anti-tubulin and anti-vimentin as the IC probes. Conclusion: the new method of Example 2 does not interfere with the detection of intracellular Vimentin or Tubulin, either alone or simultaneously, present in either CD3 or CD4 lymphocytes, present in thawed PBMC preparations.

EXAMPLE 10

Figure 12A:
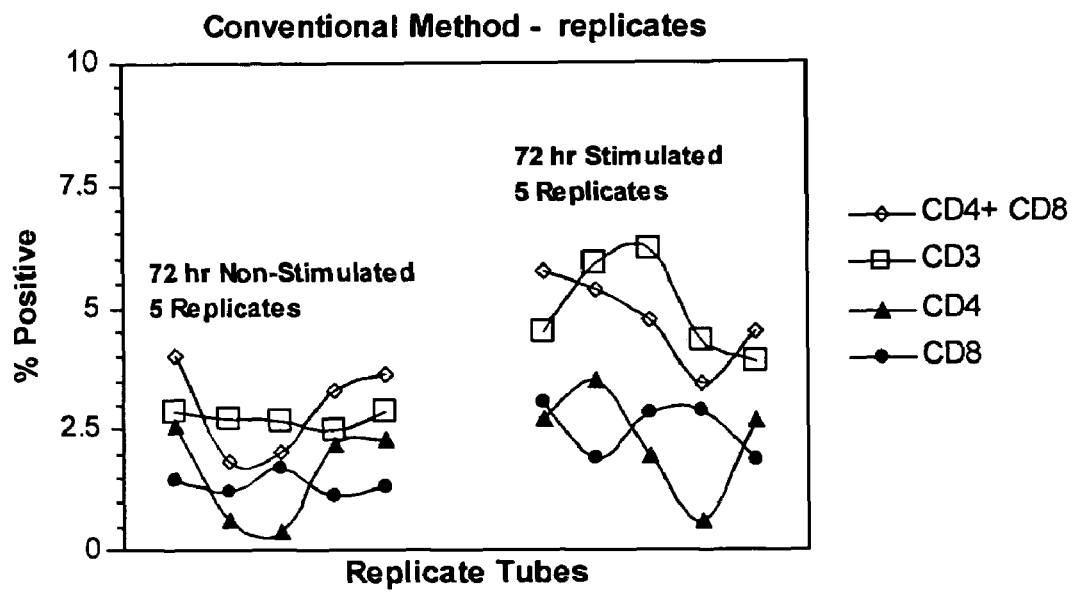
Figure 12B:
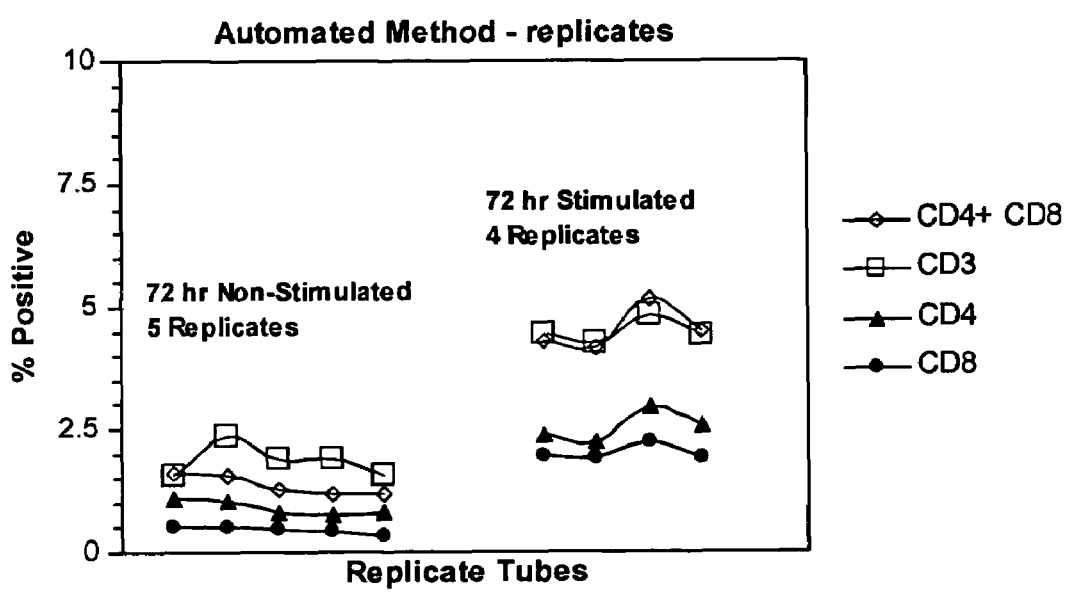

Detection of a Cytoplasmic Proliferation Antigen (CPA) in Previously Frozen and Cultured PBMCs Comparing Samples Prepared by the Methods Depicted in FIGS. 1 and 2A Peripheral Blood Mononuclear Cells (PBMCs) were prepared, frozen, and thawed according to methods known to those skilled in the art. In each of several standard fifteen milliliter culture tubes, five million PBMCs were added to 1 milliliter of traditional RPMI culture medium contained by such tubes. The RPMI culture medium was supplemented with 10% Human AB Serum. In some of the culture tubes a traditional lymphocyte stimulating agent (*Staphylococcus* Enterotoxin B, SEB, and co-stimulant anti-CD28 antibody) was added. In the remaining tubes, no such stimulating agent was added. The culture tubes were then placed in a LabPack incubator set at 37° C. and supplemented with 5% $CO_2$ for 72 hours. As in the conventional preparation method described in EXAMPLE 1, the manufacturer's recommended doses (typically 10 microliters per test) of probes specific to certain surface antigens of interest were manually pipetted into each of twenty different 12×75 mm test tubes. The surface probes were the following three fluorochrome-labeled antibodies: i)CD3 conjugated with a phycoerythrin cyanine-7 tandem dye (PC7) dye, an antibody specific to the CD3 antigen present on the surface of T-lymphocytes; ii) CD4 conjugated with a phycoerythrin cyanine-5 tandem dye (PC5), an antibody specific to the CD4 antigen present mainly on the surface of T-helper lymphocytes; and iii) CD8-conjugated with a fluorescein isothiocyanate dye (FITC), an antibody specific to the CD8 antigen present mainly on the surface of T-cytotoxic lymphocytes. A fifty microliter sample containing 250,000 72-hour, non-stimulated cultured human PBMC's was then manually pipetted into each of a first set of ten test tubes. Similarly, a fifty microliter sample containing 250,000 72-hour, stimulated cultured human PBMCs was then manually pipetted into a second set of ten test tubes. The contents of the twenty tubes were mixed by a gentle swirling of the tube. The tube contents were then incubated at room temperature for 15 minutes protected from the light. One set of ten tubes (five stimulated and five non-stimulated) was then further prepared for intracellular analysis using the conventional manual method described in EXAMPLE 1. The remaining set of ten tubes (five stimulated and five non-stimulated) were placed in a carousel-type tube holder which, in turn, was then placed onto a PrepPlus2 instrument that performed the pipetting and incubation steps (according to a modified software protocol) as depicted in FIG. 2A and described in Example 3. In this Example, the intracellular probe was 0.5 micrograms in 20 microliters of the cytoplasmic proliferation antigen (CPA) conjugated with a phycoerythrin (PE) dye. In both sample preparation methods, paraformaldehyde (PFA) at a concentration of 5.5% was used as the fixative, saponin, at a concentration of 0.7%, was used as the permeabilizing/lysing reagent. The first set of tubes was subjected to the multiple centrifugation and vortex mixing steps associated with the conventional manual method of sample preparation. The second set of tubes was subjected to only one wash step, that being carried out by the CellPrep instrument (using Protocol 2) at the end of the process. Each of the twenty tubes was then presented to a Beckman Coulter Cytomics FC500 flow cytometer utilizing RXP software, for data acquisition and analysis. The results of such analysis are summarized in the gating scheme illustrated FIGS. 11A-11F, and in the graphs of FIGS. 12A and 12B. The graphs compare the replicates of the 72 hr cultured PBMC samples stained with CD3-PC7, CD4-PC5, CD8-FITC, CPA-PE, and gated as described in FIGS. 11A-11F. PBMC were cultured in either media alone (Non-Stimulated) or in the presence of stimulating agents SEB and CD28 (Stimulated). The percent of CPA-positive expression in CD3-positive lymphocyte populations (gated from region A), the percent of CPA expression in CD3-positive-CD4-positive lymphocyte population (gated from region C), and the percent of CPA expression in CD3-positive-CD8-positive lymphocyte population (gated from region D) are shown. In FIG. 12A, the samples were prepared according to the conventional manual method (FIG. 1). In FIG. 12B, the samples were prepared according to the method of the invention, as semi-automated via the use of the PrepPlus2 and CellPrep instruments. Conclusion: the automated method described here produces CPA values in thawed PBMCs cultured for 72 hour (with or without added stimulation) which are comparable to the values obtained from the conventional method. Importantly, the automated method of the invention demonstrates substantially reduced variability between replicates as compared to the conventional method values.

EXAMPLE 11

Detection of Intracellular Cytokine TNF-alpha in Stimulated Tall-104 T Cell Line PB120 from Samples Prepared by the Methods Depicted in FIGS. 1 and 2A Tall-104 is a cell line derived from human T cells from a patient diagnosed with Acute Lymphocytic Leukemia. These cells constitutively express low levels of cytokines (Interferon-gamma, IFNg, and Tumor Necrosis Factor-alpha, TNFa) and increase the levels upon stimulation in culture. In this example, five million Tall-104 cells were placed in five-hundred microliters of Isocove's Modified Dulbecco's Medium with 20% Fetal Calf Serum, in traditional fifteen milliliter culture tubes either with (stimulated) or without (non-stimulated) traditional lymphocyte stimulating agents (CD3 antibody bound to Dextran, CD28 antibody, and IL-2 cytokine). The culture tubes were then placed in a LabPack incubator set at 37° C. and supplemented with 5% $CO_2$ for sixty minutes. Ten microliters of Brefeldin-A containing a dose sufficient to prevent cytokine secretion was added to each culture. The tubes were replaced in the incubator for an additional five hours. As in the conventional preparation method (EXAMPLE 1), the manufacturer's recommended dose of a fluorochrome-labeled surface antigen probe (10 microliters per test of antibody CD3 conjugated with a fluorescein isothiocyanate (FITC) dye, specific to the CD3 antigen present on the surface of T-lymphocytes) was manually pipetted into each of twelve different 12×75 mm test tubes. A fifty microliter sample containing 500,000 non-stimulated cultured Tall-104 cells was then manually pipetted into each of six test tubes. A fifty microliter sample containing 500,000 stimulated cultured Tall-104 cells was then manually pipetted into another set of six test tubes. The contents of the twelve tubes were mixed by a gentle swirling of the tube. The tube contents were then incubated at room temperature for 15 minutes protected from the light. Six of the tubes (three un-stimulated and three stimulated) were then prepared manually according to the conventional method described in EXAMPLE 1 and using 20 microliters of either the isotype probe (in two tubes, one un-stimulated and the other stimulated) or the specific intracellular cytokine probe (TNFa) both conjugated with a phycoerythrin (PE) dye (in the other four tubes, two un-stimulated and the other two stimulated). The remaining six tubes were placed in a carousel-type tube holder, which was then placed onto a PrepPlus2 instrument that performed the pipetting and incubation steps (according to a modified software protocol) as described in EXAMPLE 2. 25 microliters of paraformaldehyde (PFA) at a concentration of 5.5% were pipetted into each tube and incubated for 20 minutes. Then, 20 microliters of either the isotype probe or the specific intracellular cytokine probe (TNFa) both conjugated with a phycoerythrin (PE) dye, was added to each tube immediately followed by the addition of 100 microliters of saponin, at a concentration of 0.7%. The tubes were incubated for 45 minutes. Thereafter, 600 microliters of IsoFlow were added to each tube. The carousel was then transported to a CellPrep instrument, where each tube in turn was filtered according to a standard protocol (number 2) shipped with the instrument. Each of the twelve tubes was then presented to a Beckman Coulter Cytomics FC500 flow cytometer utilizing RXP software for data acquisition and analysis. The results of such analysis are summarized in FIGS. 13A-13D.

The overlay plots of FIGS. 13C and 13D compare the TNFa expression in CD3 positive Tall-104 cells for four different samples gated as shown in FIGS. 13A and 13B. In FIG. 13B, the lower threshold level E is determined from the sample containing the isotype probe, as explained EXAMPLE 4 above. "Conventional" indicates that samples were prepared as in EXAMPLE 1, and "Automated" indicates that samples were prepared as described in EXAMPLE 2 and illustrated in FIG. 2A. "Isotype" refers to those samples stained with CD3-FITC and Isotype-PE. "TNFa" refers to those samples stained with CD3-FITC and TNFa-PE. Conclusion: the method of the invention is comparable to the conventional method in preparing cell samples for detection of intracellular TNFa cytokine inside CD3 positive stimulated Tall-104 cells.

EXAMPLE 12

Indirect Detection of Intracellular Defensin Molecules Present in the Neutrophil Cell Population of Whole Blood The monoclonal antibody, anti-CD15, conjugated with a fluorescein isothiocynate (FITC) dye was manually pipetted into each of eight different 12×75 mm test tubes. The CD15 antigen molecule is present on the surfaces of neutrophils, eosinophils, monocytes, macrophages, mast cells, and normal myeloid precursor cells. A fifty microliter sample of heparinized whole blood obtained by venipuncture from a human subject was then manually pipetted into each of the test tubes and the contents of each tube were mixed by a gentle swirling of the tube. The tube contents were incubated at room temperature for 15 minutes protected from the light. Four of the tubes were prepared manually according to the conventional method described in Example 1 with the intracellular probes being five microliters of PBS containing two micrograms of either an appropriate purified isotype antibody (e.g. mouse IgG) in two tubes, or a purified anti-defensin (type HNP-B) monoclonal antibody in two tubes. Defensins are small cationic anti-microbial proteins and are principal constituents of human neutrophils. The spatially separated hydrophobic and charged (cationic) residues allow the peptides to insert into phospholipid membranes and preferentially disrupt bacterial membranes that are rich in negatively charged phospholipids). There was an addition to the method described in EXAMPLE 1 of the following two steps immediately following step (m) in FIG. 1 and before step (n); i.e., 100 microliters of PBS containing four microliters of a secondary detection probe (a sheep antibody specific to mouse antibody Fab fragment (SAM) conjugated to PE from Chemicon International Company) were added to the pellet resulting from the last centrifugation step, followed by an additional 15 minute incubation period.

The remaining four tubes, containing the incubated anti-CD15 and whole blood, were placed in a carousel-type tube holder which was then placed onto a PrepPlus2 instrument that performed the pipetting and incubation steps according to Example 2 with the intracellular probes are the same type as described above, and except there were an additional three steps inserted prior to the carousel transfer to a CellPrep instrument: After the addition of 600 microliters of IsoFlow, the four tubes were removed from the carousel and placed in a Beckman J6B centrifuge for 5 minutes at 500×g force (a quick-spin). The majority of the supernatant was aspirated and 100 microliters of PBS containing the secondary probe was manually pipetted into each of the four tubes. The tubes were swirled gently to resuspend the cell pellets, and incubated for 45 minutes immediately followed by the manual addition of 900 microliters of PBS to each of the four tubes. The tubes were replaced on the carousel and transported to a CellPrep instrument, where each tube in turn was filtered according to a standard protocol (number 2) shipped with the instrument. Each of the eight tubes was presented then to a Beckman Coulter Cytomics FC500 flow cytometer utilizing RXP software for data acquisition and analysis. The results of such analysis are summarized in FIGS. 14A-14C.

The overlay plot of FIG. 14C compares four different samples gated as indicated described in FIGS. 14A and 14B show defensin expression in the CD15-positive granulocyte populations. Manual indicates that samples were prepared as in Example 1 (with exceptions noted above). Automated indicates that samples were prepared as described in this Example 2 (with exceptions noted above). Isotype indicates the samples were stained with CD15-FITC and isotype plus the secondary probe SAM-PE. Defensin indicates the samples were stained with CD15-FITC and anti-Defensin probe plus the secondary probe SAM-PE. Conclusion: the automated method described here is feasible but not optimized for the indirect detection of intracellular Defensin inside CD15 positive granulocytes present in whole blood.

EXAMPLE 13

Detection of Intracellular MPO Molecule Present in the Neutrophil Cell Population of Whole Blood The monoclonal antibody, anti-CD15, conjugated with a fluorescein isothiocynate (FITC) dye was manually pipetted into each of eight different 12×75 mm test tubes. The antibody was a monoclonal antibody specific to the CD15 surface antigens present on neutrophils, eosinophils, monocytes, macrophages, mast cells, and normal myeloid precursor cells. A fifty microliter sample of heparinized whole blood obtained by venipuncture from a human subject was then manually pipetted into each of the test tubes and the contents of each tube were mixed by a gentle swirling of the tube. The tube contents were then incubated at room temperature for 15 minutes protected from the light. Four of the tubes were prepared manually according to the conventional method described in EXAMPLE 1, and four tubes were placed in a carousel-type tube holder, which was then placed onto a PrepPlus2 instrument that performed the pipetting and incubation steps described in Example 2 and shown in FIG. 2A. An intracellular probe, myeloperoxidase (MPO), conjugated with a phycoerythrin (PE) dye, was pipetted into two tubes of each four tube set and prepared by each method; MPO is an intracellular antigen found in the azurophilic granules of neutrophils. It is useful in diagnosing leukemia. Similarly, an isotype probe, also conjugated with a phycoerythrin (PE) dye, was added to the remaining two tubes of each set, and the samples were again prepared by each method. Each of the eight tubes was then presented to a Beckman Coulter Cytomics FC500 flow cytometer utilizing RXP software for data acquisition and analysis. The results of such analysis are summarized in FIGS. 15A-15C. The overlay plot of FIG. 15C compares four different samples gated as indicated in FIGS. 15A and 15B. MPO expression in CD15 positive granulocyte populations. "Manual" indicates that samples were prepared as in EXAMPLE 1, and "Automated" indicates that samples were prepared as described in this EXAMPLE 2, as semi-automated through the use of the PrepPlus2 and CellPrep instruments. Isotype indicates the samples were stained with CD15-FITC and Isotype-PE. MPO indicates the samples were stained with CD15-FITC and MPO-PE. Conclusion: the sample preparation method of the invention is comparable to the conventional method in detecting the percentage of CD15 positive-granulocytes expressing intracellular MPO present in whole blood.

EXAMPLE 14

Detecting a Cytoplasmic Cytokine in a Previously Frozen and Cultured PBMC Cell

Comparing the Sample-Preparation Methods of FIGS. 1 and 2A

Peripheral Blood Mononuclear Cells (PBMCS) were prepared, frozen, and thawed according to methods known to those skilled in the art. Fifteen million PBMCs were placed in 1.5 milliliters of traditional RPMI culture medium supplemented with 10% Human AB Serum, and divided equally among three traditional fifteen milliliter culture tubes. The culture tubes contained traditional lymphocyte stimulating agents (*Staphylococcus* Enterotoxin B, SEB, and co-stimulant anti-CD28 antibody) and were labeled "stimulated." The three culture tubes were placed in a LabPack incubator set at 37° C. and supplemented with 5% $CO_2$ for 1.5 hours. Five microliters of Brefeldin-A containing 2.5 micrograms (a dose sufficient to prevent cytokine secretion) was added then to each of the three culture tubes. The tubes were replaced in the incubator for an additional 15.5 hours. The contents of the three tubes containing the stimulating agents were pooled into single tube. A fifty microliter sample from the stimulated pooled culture tube, each containing 500,000 cells, was placed into each of four 12×75 mm tubes. The samples contained by two of the four tubes were further prepared according to the conventional method described in EXAMPLE 1, with the surface probes being the manufacturer's recommended doses (typically 10 microliters per test) of the following four fluorochrome-labeled monoclonal antibodies: (i) CD8 conjugated with a fluorescein isothiocyanate (FITC) dye, specific to the CD8 antigen present on the surface of T-cytotoxic lymphocytes; (ii) CD69 conjugated to phycoerythrin-cyanine 5 tandem dye (PC5), specific to the surface antigen present on most activated lymphocytes); (iii) CD4 conjugated with a phycoerythrin-Texas red (ECD) tandem dye, specific to the CD4 antigen present on the surface of T-helper lymphocytes; and (iv) CD3 conjugated to phycoerythrin-cyanine 7 (PC7) tandem dye, specific for the CD3 antigen present on all T lymphocytes). The intracellular probe used was the manufacturer's recommended dose of twenty microliters of the specific intracellular cytokine probe for tumor necrosis factor-alpha (TNFa); this probe was conjugated with a phycoerythrin (PE) dye. The wash buffer was a PBS solution containing 0.1% sodium azide and 2% fetal calf serum (FCS). All other reagents were as described in EXAMPLE 1. Thus, two samples were prepared for intracellular analysis using the method of the prior art.

Figure 16A:
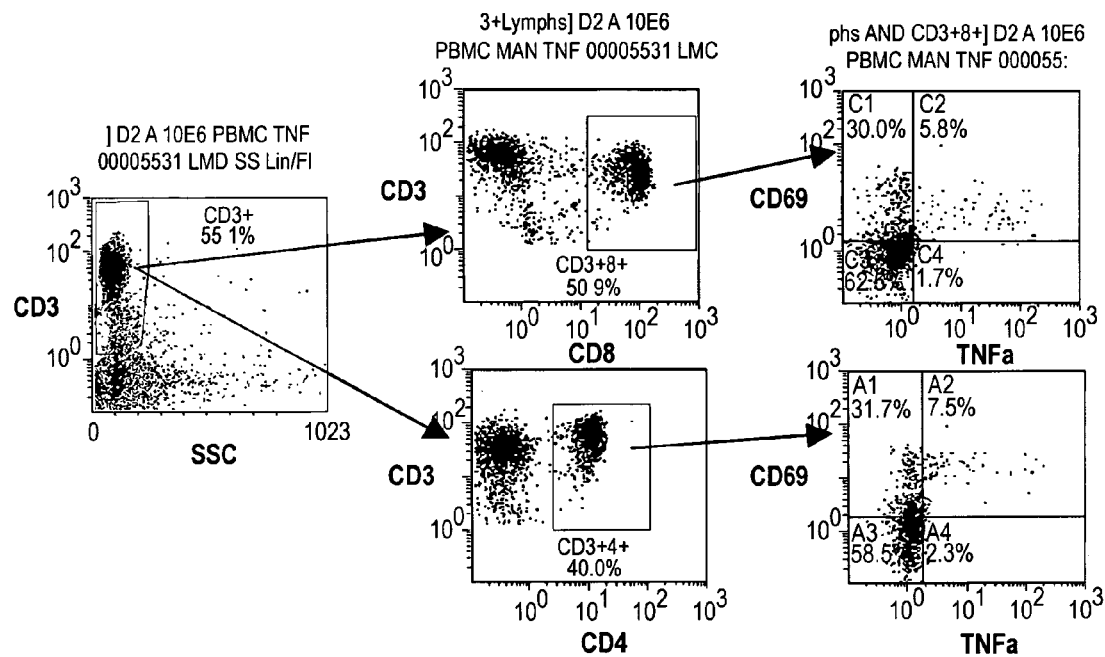
Figure 16B:
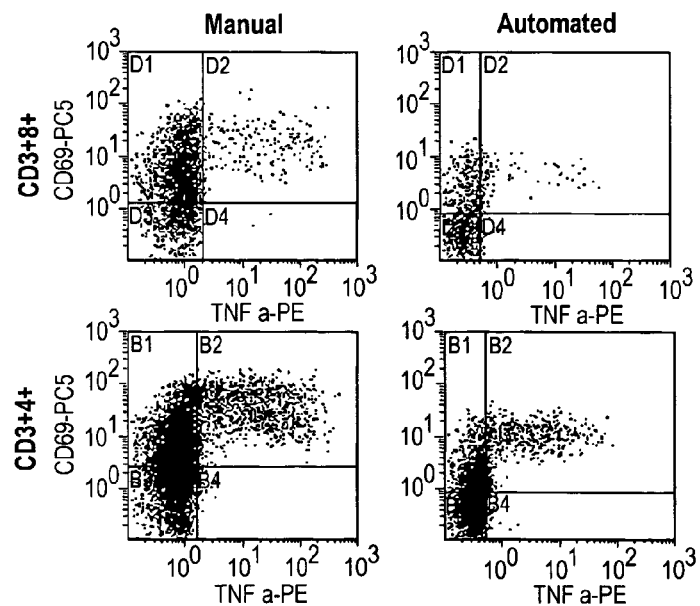

Into the remaining two tubes, each containing 50 microliters of stimulated PBMC's, the surface marker probes noted above were added. The contents of the two tubes were mixed by a gentle swirling of the tubes. The tube contents were then incubated at room temperature for 15 minutes protected from the light. The tubes were placed in a carousel-type tube holder, which was then placed onto a PrepPlus2 instrument that performed the pipetting and incubation steps (according to a modified software protocol) as described in Example 3 with reference to FIG. 2A. The specific intracellular cytokine probe used was for tumor necrosis factor-alpha (TNFa). This probe was conjugated with a phycoerythrin (PE) dye. The carousel was then transported to a CellPrep instrument, where each tube in turn was filtered according to a standard protocol (number 2) shipped with the instrument. Each tube prepared according to the conventional method and the new method described here was then presented to a Beckman Coulter Cytomics FC500 flow cytometer utilizing RXP software for data acquisition and analysis. The results of such analysis are summarized in the scattergrams of FIG. 16A and 16B. The thawed and stimulated PBMC samples were analyzed for TNFa production via the Conventional and New Method of sample preparation. The detected percentage of CD3+CD4+CD69+TNFa+ and CD3+CD8+CD69+TNFa+ quadruple-positive are shown in TABLE 3 below. The gating scheme is shown in the scattergrams of FIG. 16A, and the scattergrams of FIG. 16B represent events gated on either CD3+CD8+ (top) or CD3+CD4+ (bottom) populations. The scattergram displays are TNFa-PE (x-axis) vs. CD69-PC5 (y-axis). It is apparent that the new method described here provides nearly the same values as the conventional method for thawed cultured PBMCs.

TABLE 3

|  | Conventional Method | New Method |
|---|---|---|
| % CD3+CD4+CD69+TNFa+ | 12.8 | 10.7 |
| % CD3+CD8+CD69+TNFa+ | 8.4 | 7.7 |

EXAMPLE 15

Detecting a Cytoplasmic Cytokine in a PBMC Cell Sample that has been Frozen and Cultured with Vaccine Antigen; New v. Conventional Sample Prep Methods Peripheral Blood Mononuclear Cell (PBMC) cells were obtained from a donor vaccinated with a particular vaccine antigen. These cells were then frozen and thawed according to methods known to those skilled in the art. Fifteen million of the thawed PBMCs were placed in 3 milliliters of traditional RPMI culture medium supplemented with 10% Human AB Serum, and divided equally among six traditional fifteen milliliter culture tubes. Two culture tubes contained traditional lymphocyte stimulating agents (*Staphylococcus* Enterotoxin B, SEB, and co-stimulant anti-CD28 antibody) and were labeled "SEB +CD28"; two other culture tubes labeled "Vaccine Ag" contained an amount of vaccine antigen sufficient to stimulate the PBMC cells from the vaccinee; and the two remaining tubes did not contain any stimulating agents and were labeled "Non-Stim". The six culture tubes were then placed in a LabPack incubator set at 37° C. and supplemented with 5% $CO_2$ for 1.5 hours. Five microliters of Brefeldin-A containing 2.5 micrograms (a dose sufficient to prevent cytokine secretion) was added then to each of the six culture tubes. The tubes were replaced in the incubator for an additional 16 hours. Each of the two similar cultures (i.e. SEB, Stimulated and Non-Stimulated) were pooled into single 75 mm specimen tubes with pierceable caps. These specimen tubes were labeled SEB, Vaccine, or Non-Stimulated. Fifty microliter samples, each containing 250,000 cells, were pipetted from of each of the three pooled culture tubes, and were dispensed into three 12×75 mm tubes. These samples were then further prepared according to the conventional method described in EXAMPLE 1 with the four surface probes being those described in EXAMPLE 14 (i.e., CD8-FITC, CD69-PC5, CD4-ECD, CD3-PC7). The intracellular probe used was the manufacturer's recommended dose of twenty microliters of the specific intracellular cytokine probe interferon-gamma (IFNg) conjugated with a phycoerythrin (PE) dye. The wash buffer was a PBS solution containing 0.1% sodium azide and 2% fetal calf serum (FCS).

Figure 17A:
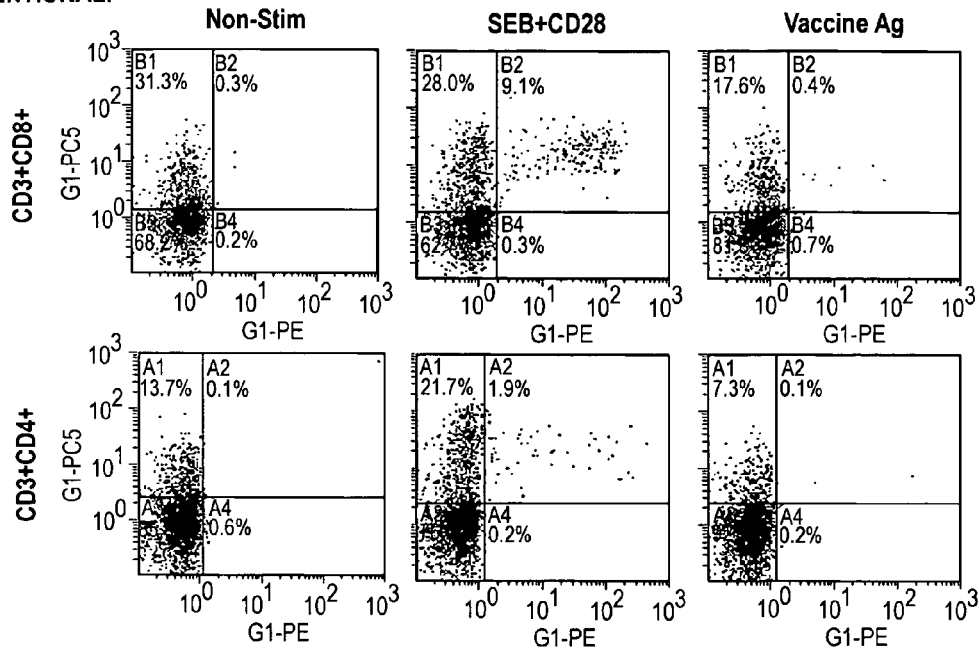
Figure 17B:
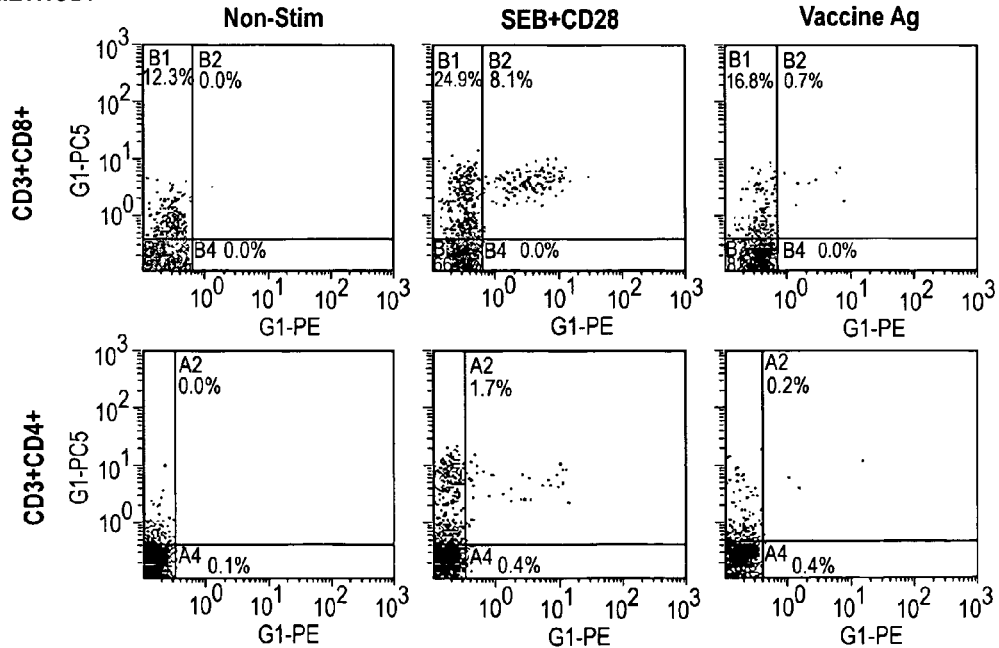

The three pooled culture tubes were then placed into positions 1-3 of the specimen rack of the PrepPlus2 pipetting instrument. The commercial software PanelDef, supplied with the instrument, was used to create a protocol to automatically pipet the same volumes of surface antibodies described above into three 12×75 mm test tubes supported in a carousel-type holder. 50 microliters, each containing 250,000 cells, were then transferred from each of the three specimen tubes into the 12×75 mm test tubes containing the surface antibodies. The tubes in the carousel were incubated at room temperature for 15 minutes (without removing from the PrepPlus2). The modified software to perform the new method described in Example 3 was used. The specific intracellular cytokine probe in this example was interferon gamma (IFNg) conjugated with a phycoerythrin (PE) dye. The carousel was transported to a CellPrep instrument, where each tube in turn was filtered according to a standard protocol (number 2) shipped with the instrument. Each of the six tubes, three being prepared according to the conventional method and three being prepared according to the new method described here, was presented to a Beckman Coulter Cytomics FC500 flow cytometer utilizing RXP software for data acquisition and analysis. The results of such analysis are summarized in TABLE 4 and in FIGS. 17A and 17B. In FIG. 17A, the results are shown for each of the three cultured samples prepared by the conventional manual method of EXAMPLE 1. FIG. 17B shows the similar results attained using the method of the invention (shown in FIG. 2A). In both figures, the scattergrams represent events gated on either CD3+CD8+ (top) or CD3+CD4+ (bottom) populations. Histogram displays are IFNg-PE (x-axis) vs. CD69-PC5 (y-axis). The percentage of CD3+CD4+CD69+IFNg+ and CD3+CD8+CD69+IFNg+ quadruple-positive lymphocytes are recorded in the table. Conclusion: It is apparent that the new method described here provides better values than the conventional method for thawed PBMCs cultured with a vaccine antigen, due to the lower values present in the non-stimulated samples (background). The lower background is due to the new method reducing the degree of dispersion of events plotted on the histograms.

TABLE 4

| | Manual | | | Automated | | |
|---|---|---|---|---|---|---|
| | NonStim | SEB+ CD28 | Vaccine Ag | NonStim | SEB+ CD28 | Vaccine Ag |
| % CD3+8+69+ IFNg+ | 0.34 | 9.06 | 0.38 | 0.04 | 8.08 | 0.68 |
| % CD3+4+69+ IFNg+ | 0.14 | 1.87 | 0.08 | 0.03 | 1.66 | 0.25 |

EXAMPLE 16

Figure 18:
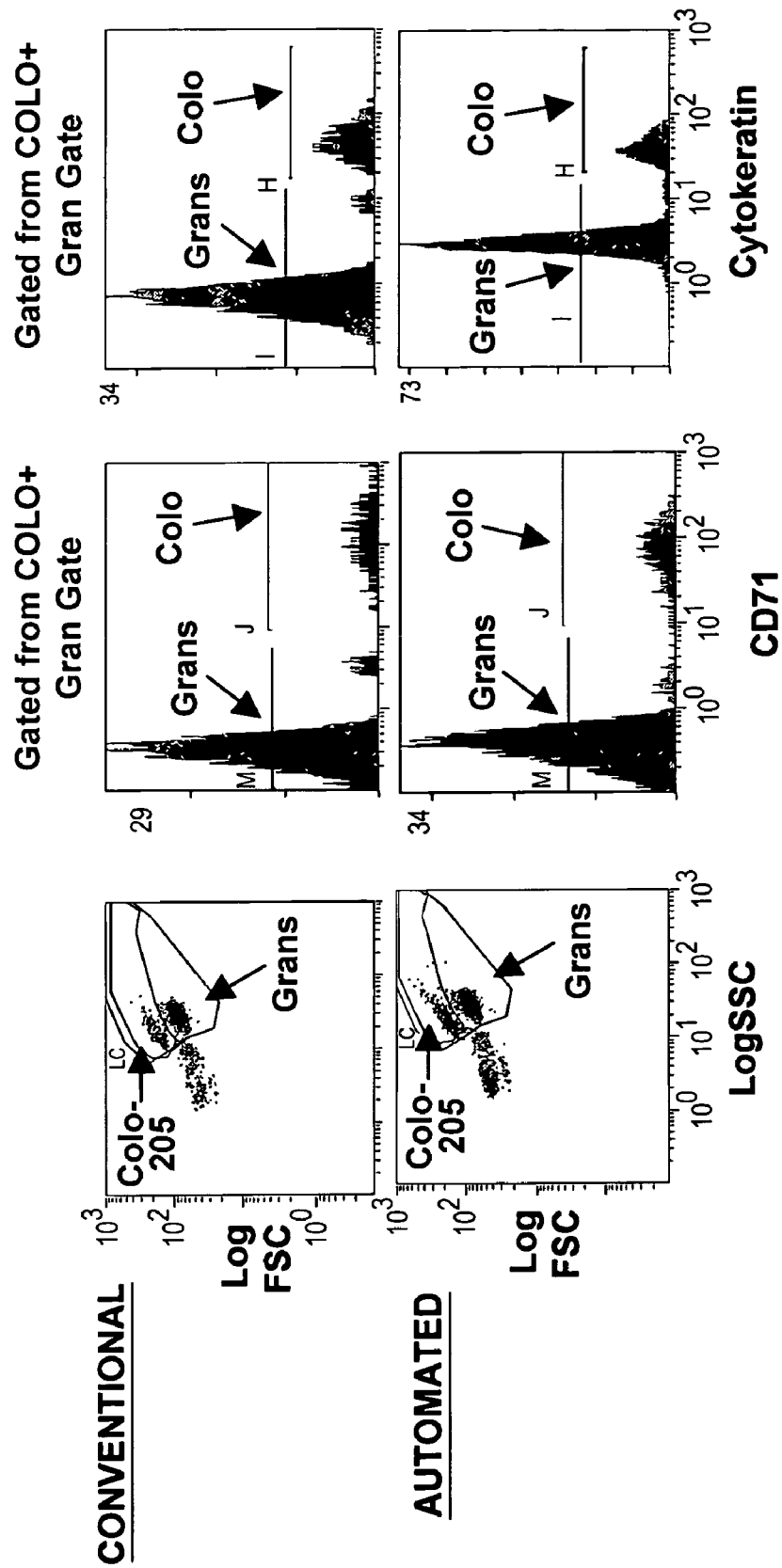

Detection of Cytokeratin-Positive Cells in a Mixture of Whole Blood and a Cell Line Comparing the Methods Depicted in FIGS. 1 and 2B Colo-205 is an epithelial cell line derived from ascites fluid of a patient diagnosed with colon adenocarcinoma, which grows in culture as a mixture of suspended and adhered cells. These cells express intracytoplasmic cytokeratin (which make up a type of intermediate filaments present in epithelial cells), and express CD71 (the human transferring receptor present on the majority of human tumor cell lines and normal peripheral blood monocytes) on the cell surface. When these cells are diluted into human whole blood and prepared for flow cytometry, they are distinguished from white blood cell (WBC) populations based on light scattering properties (FIG. 18). Four 12×75 mm staining tubes were prepared containing a fifty microliter sample of whole blood obtained by venipuncture from a normal donor containing Colo-205 cells. Duplicate 12×75 mm staining tubes were prepared according to the conventional method described in EXAMPLE 1 with the surface probe being 20 ul of anti-CD71 conjugated to phycoerythrin (PE) dye, and the intracellular probe used was 20 ul of anti-Cytokeratin antibody conjugated with a fluorescein isothiocyanate (FITC) dye. The wash buffer was a PBS solution containing 0.1% sodium azide. The other two staining tubes were prepared with the modified method of this invention shown in FIG. 2B and described as follows: 20 ul of the probe for CD71 surface molecule and 20 ul of the intracellular cytokeratin molecule probe, were pipetted simultaneously into each of two 12×75 tubes placed in a carousel-type tube holder. The carousel was then placed onto a PrepPlus2 instrument and incubated for fifteen minutes at room temperature. The PrepPlus2 then performed the pipetting and incubation steps (according to a modified software protocol) described here. To each tube in turn was added one-hundred microliters of a paraformaldehyde (PFA) solution at a concentration of 5.5%, one-hundred microliters of a red blood cell lysing reagent (1× concentration of ammonium chloride solution (Beckman Coulter, Inc. IOTest3 Lysing Reagent)), and one-hundred microliters if a saponin solution at a concentration of 0.7%. The tubes were held at room temperature for 20 minutes. Thereafter, 600 microliters of PBS were added to each tube. The carousel was then transported to a CellPrep instrument, where each tube in turn was filtered with the standard IsoFlow reagent according to a standard protocol (number 2) shipped with the instrument. Each of the four tubes was then presented to an EPICS XL-MCL flow cytometer utilizing EXPO-ADC software for data acquisition and analysis. The results of such analysis are summarized in FIG. 18. The top three histograms in FIG. 18 represent a sample prepared according to the conventional method described in EXAMPLE 1, and the lower three histograms represent a sample prepared according to the method of this invention (semi-automated) as shown in FIG. 2B. Visual inspection of both of the Log SSC vs. Log FSC scattergrams show that the light scattering properties of Colo-205 cells are sufficiently different from granulocytes to provide a separate population. The four histograms were gated from the appropriate log FS vs. log SS gate comprising both the Colo-205 cells and the granulocyte population. The dark black line analysis regions ("Grans") drawn on each histogram represent the cells that are negative for both CD71 and Cytokeratin. The lighter black line analysis regions ("Colo") represent the cells that are positive for both CD71 and Cytokeratin. They have identified as Granulocytes and Colo-205 respectively, by an analysis method commonly used by those skilled in the art which used color back-gating to show that the cells in the "Grans" histogram regions only showed in the Grans region of the light scatter scattergram, and the cells in the "Colo" histogram regions only showed in the Colo-205 region of the light scatter scattergram. The comparable results obtained from the conventional and automated methods demonstrate that the semi-automated sample preparation method can be used to detect circulating colon carcinoma cells (Colo-205) present in peripheral blood by virtue of their CD71 and Cytokeratin expression.

EXAMPLE 17

Figures 19A, 19B:
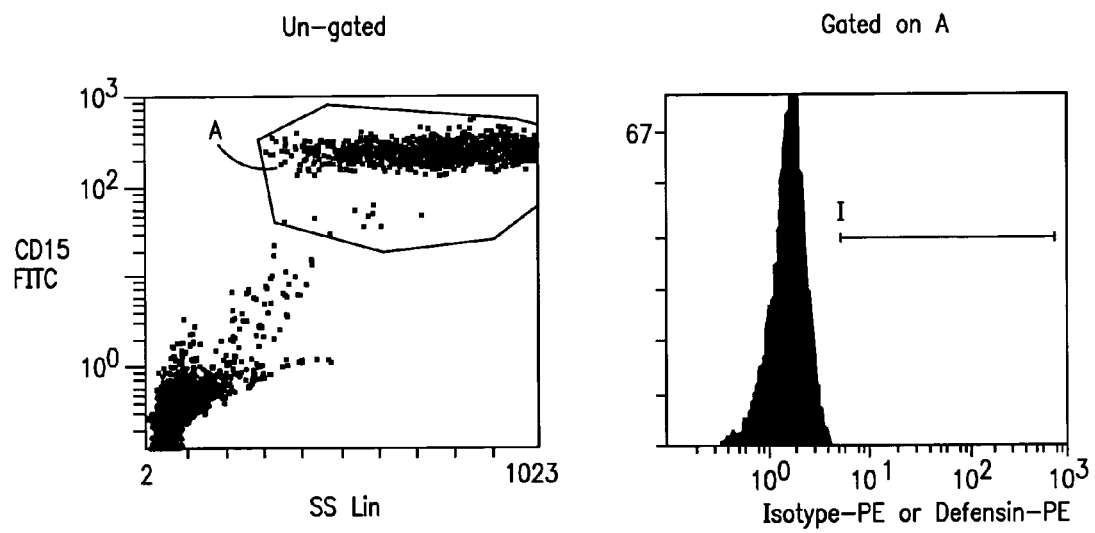
Figure 19C:
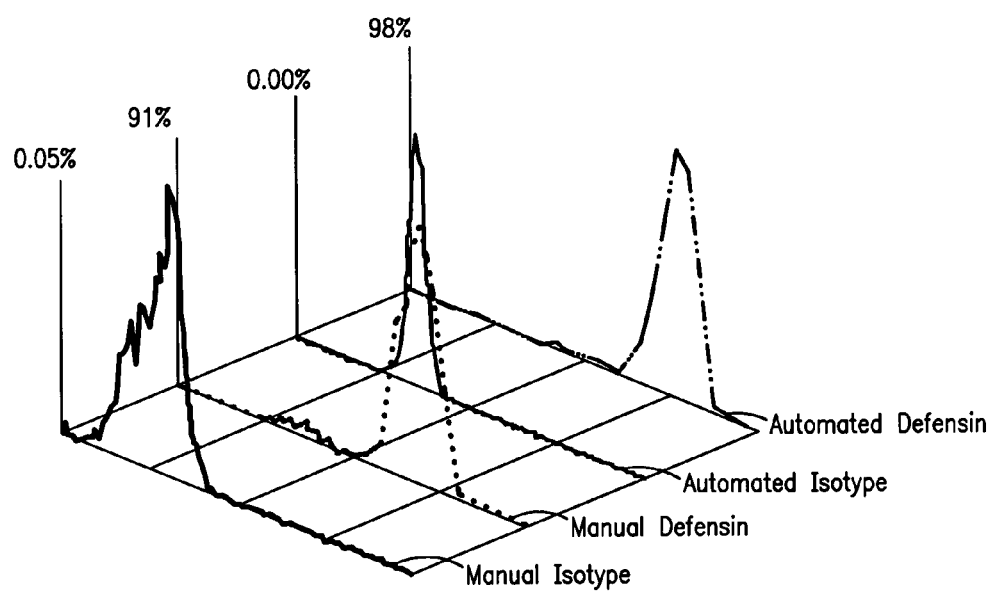

Direct Detection of Intracellular Defensin Molecules Present in the Neutrophil Cell Population of Whole Blood The fluorochrome-labeled antibody CD15 conjugated with a fluorescein isothiocynate (FITC) dye was manually pipetted into each of four different 12×75 mm test tubes. The antibody was a monoclonal antibody specific to the CD15 surface antigens present on neutrophils, eosinophils, monocytes, macrophages, mast cells, and normal myeloid precursor cells. A fifty microliter sample of EDTA whole blood obtained by venipuncture from a human subject was then manually pipetted into each of the test tubes and the contents of each tube were mixed by a gentle swirling of the tube. The tube contents were then incubated at room temperature for 15 minutes protected from the light. Two of the tubes were then prepared manually according to the conventional method described in EXAMPLE 1 and the remaining two tubes were placed in a carousel-type tube holder, which was then placed onto a PrepPlus2 instrument that performed the pipetting and incubation steps as in EXAMPLE 3. In both of these methods the intracellular markers were either the appropriate isotype antibody (e.g. mouse IgG1) conjugated to phycoerythrin (PE) dye (added to one of the two tubes), or 20 microliters containing 0.25 micrograms of anti-Defensin HNP-B antibody conjugated to phycoerythrin (PE) dye (added to the remaining one of two tubes). Each tube was then presented to a Beckman Coulter Cytomics FC500 flow cytometer utilizing RXP software for data acquisition and analysis. The results of such analysis are summarized in FIGS. 19A-19C. The gating scheme is shown in FIGS. 19A and 19B. The overlay plot of FIG. 19C compares the four different samples showing the defensins expression in the CD15-positive granulocyte population, as obtained from samples prepared according to the conventional "Manual" method, and the "Automated" method of the invention, as semi-automated through the use of the PrepPlus2 and Cell-Prep instruments. Isotype indicates the samples were stained with CD15-FITC and Isotype-PE. Defensin indicates the samples were stained with CD15-FITC and anti-Defensin-PE. Conclusion: The method described in Example 2 is feasible for the intracellular detection of defensin in CD15+ white blood cells.

From the above Examples, it is apparent that the new methods of the invention, though considerably less complex than the conventional prior art methods, provide equally effective test results for a wide variety of different types of cell samples and intracellular antigens of interest. This is true whether the cell samples be fresh or frozen. Most importantly, the sample preparation methods of the invention provide substantially more repeatable results, especially when fully automated, as is achieved with the instrument systems described below.

Figure 20:
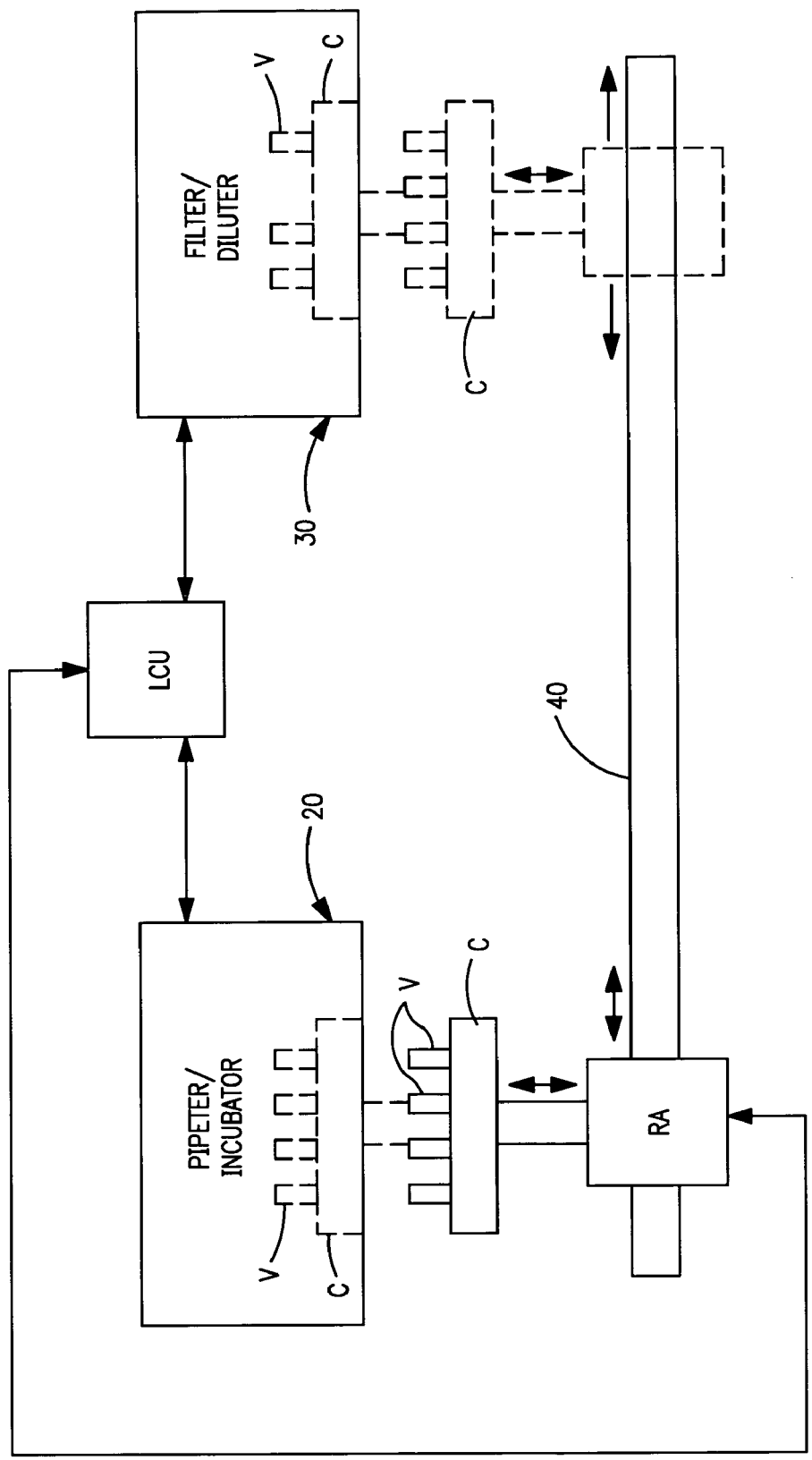
FIG. 20 is a schematic illustration of a preferred automated instrument system for automatically carrying out the cell sample preparation method of the invention.

Referring now to the schematic illustration of FIG. 20, a preferred instrument system adapted to carry out the sample-preparation method of the invention fully automatically is shown as comprising a pipeter/incubator component 20, a filter/diluter component 30, a robotic arm component RA and a microprocessor-controlled logic and control unit LCU. The latter controls the internal operation of these components, as well as their interaction in carrying out the method of the invention. Preferably, the pipeter/incubator component is a slightly modified version of the above-noted Beckman Coulter PrepPlus2 pipetting and diluting instrument, and component 30 is the above-noted Beckman Coulter CellPrep cell-washing and diluting instrument. The basic constructional and operational details of these instruments are described in their respective Operator's Manuals, the disclosures of which are incorporated herein by reference.

The conventional PrepPlus2 instrument (component 20) is a microprocessor-controlled pipetting and incubating instrument that generally includes a housing for supporting (i) a rack of cell sample tubes, each tube containing a cell sample that is to be prepared for analysis, e.g., for flow cytometric analysis; (ii) a rack of various individual reagent bottles that contain the reagents (e.g., lyse, diluents, probes, etc) necessary to prepare a cell sample in accordance with an embedded program that has been selected on a touch screen or the like, (iii) a carousel C containing a plurality (e.g., 32) of reaction vessels V (referred to as "daughter tubes") in which the cell samples are to be prepared for analysis, and (iv) and a single X/Y/Z-driven pipeter that serves to selectively move among the sample tubes and reagent bottles to aspirate cell samples and reagents therefrom, and to dispense the same into the appropriate reaction vessels. The PrepPlus2 instrument also includes a supply of various diluents for suitably diluting the cell sample and for cleansing the aspiration probe between successive operations. The internal microprocessor is programmed to control the sequence of the pipetting operations, the X-Y-Z movement of the pipeter, and the liquid volumes aspirated and dispensed. It also controls the timing between successive liquid-dispensing operations to precisely control the various incubation times of the contents of the reaction vessels, and it can be programmed to control the ambient temperature of the pipeter housing as well.

In accordance with this aspect of the invention, the reagent rack of the PrepPlus2 instrument has been modified to receive bottles of those reagents (fixative, permeabilizer, lyse, cell surface probes, intracellular probes and buffers) required to carry out a particular intracellular sample-preparation method of interest, e.g., as described above and shown in FIGS. 2A and 2B as steps (a) through (e). Further, the internal logic and control unit that normally operates to control the operation of the PrepPlus2 instrument alone has been programmed to not only carry out the sequence and timing of steps (a) through (e) shown in FIGS. 2A and 2B, but also to control the sequence of operation of the entire instrument system. Thus, while LCU is shown as a separate component in FIG. 20, it is actually housed within component 20. It may, however, be housed in any one of the three major components, 20, 30, or RA.

Still referring to FIG. 20, the robotic arm RA is preferably the programmable robotic arm system made and sold by Beckman Coulter Inc. under the trademark ORCA. It operates under the control of the LCU to reach within the housing of the pipetting/incubator component to access and withdraw a carousel C of reaction vessels V on which steps (a) through (e) of the above process have been performed. The robotic arm then transports such carousel along a track 40 to the filter/diluter component 30 where it presents the carousel to a rotatably driven hub that supports the carousel for rotation. As indicated above, component 30 is preferably an unmodified version of the CellPrep instrument which contains several embedded protocols according to which cell samples presented to it are washed and diluted. The CellPrep instrument operates under its own internal program to rotate a received carousel of reaction-vessels about its central vertical axis to sequentially present each of the individual reaction vessels beneath a single aspiration probe. Such probe acts, under the control of the internal microprocessor, to move vertically into a reaction vessel, to aspirate the sample within the reaction vessel, and to convey the aspirated sample into the interior of the above-mentioned microporous (semi-permeable) hollow fiber where the sample is filtered to exclude interferants. After filtering, the cells of interest remain within the hollow filtering fiber, and a predetermined volume of diluent, e.g., IsoFlow, is pumped through the fiber to simultaneously flush the cells of interest from the fiber and to dispense the cells, preferably into the same reaction vessels from whence they came. According to a preferred internal Protocol 2, this filtering/dilution process is performed twice. After the cell sample in each of the reaction vessels has been filtered and diluted in this manner, the carousel is removed from the filter, and the cell sample is presented to the flow cytometer for analysis.

The manner in which the CellPrep instrument operates to filter a cell sample can be understood with reference to FIGS. 21A-21C. As shown in the drawings, the filtering element of this instrument comprises a replaceable filter cartridge FC that is in the form of an elongated flexible tube 50 of an impervious plastic material for space-saving considerations, tube 50 is curved into a circular loop. Tube 50 contains a pair of hollow fibers 52 which extend along the tube axis. Each of the hollow fibers is made of a semipermeable material having a multitude of spaced pores of a size that will transmit particles (interferants) somewhat smaller than the cells of interest while preventing such cells from passing. The typical pore size is about 0.65 microns. The filtering cartridge has four fluid couplings C1-C4 through which (a) the hollow fibers 52 can be coupled to an aspiration probe used to withdraw the cell sample from the reaction vessel; (b) a vacuum source can be selectively coupled to the interior of tube 50 for the purpose of establishing a negative pressure by which an unfiltered cell sample will be drawn through the aspirating probe and into the hollow fibers for filtering, (c) a diluent can be applied to the fibers to flush out the filtered cell sample and return it the reaction vessel, and (d) a detergent solution can be applied to the hollow fibers for cleansing purposes following a sample-filtering cycle. FIG. 21B illustrates a cut-away portion of tube 50 showing the hollow fibers 52 therein, and FIG. 21C is a schematic illustration of the filtering process, showing the larger cells C being retained within the interior of the hollow fiber 52 while the interferants pass through the fiber wall. Further details are described from the aforementioned U.S. Patent Application Publication No. US 2002/0123154.

The instrument system illustrated in FIG. 20 is capable of providing highly repeatable sample preparations in that manual involvement is completely eliminated once the racks of cell samples and reagents are loaded into component 20 and the type of sample preparation to be performed is selected. However, it will be appreciated that this instrument system, being modular in nature, requires a relatively large space to operate. This disadvantage is overcome by the single-platform instrument shown in FIG. 22, and described below.

Figure 22:
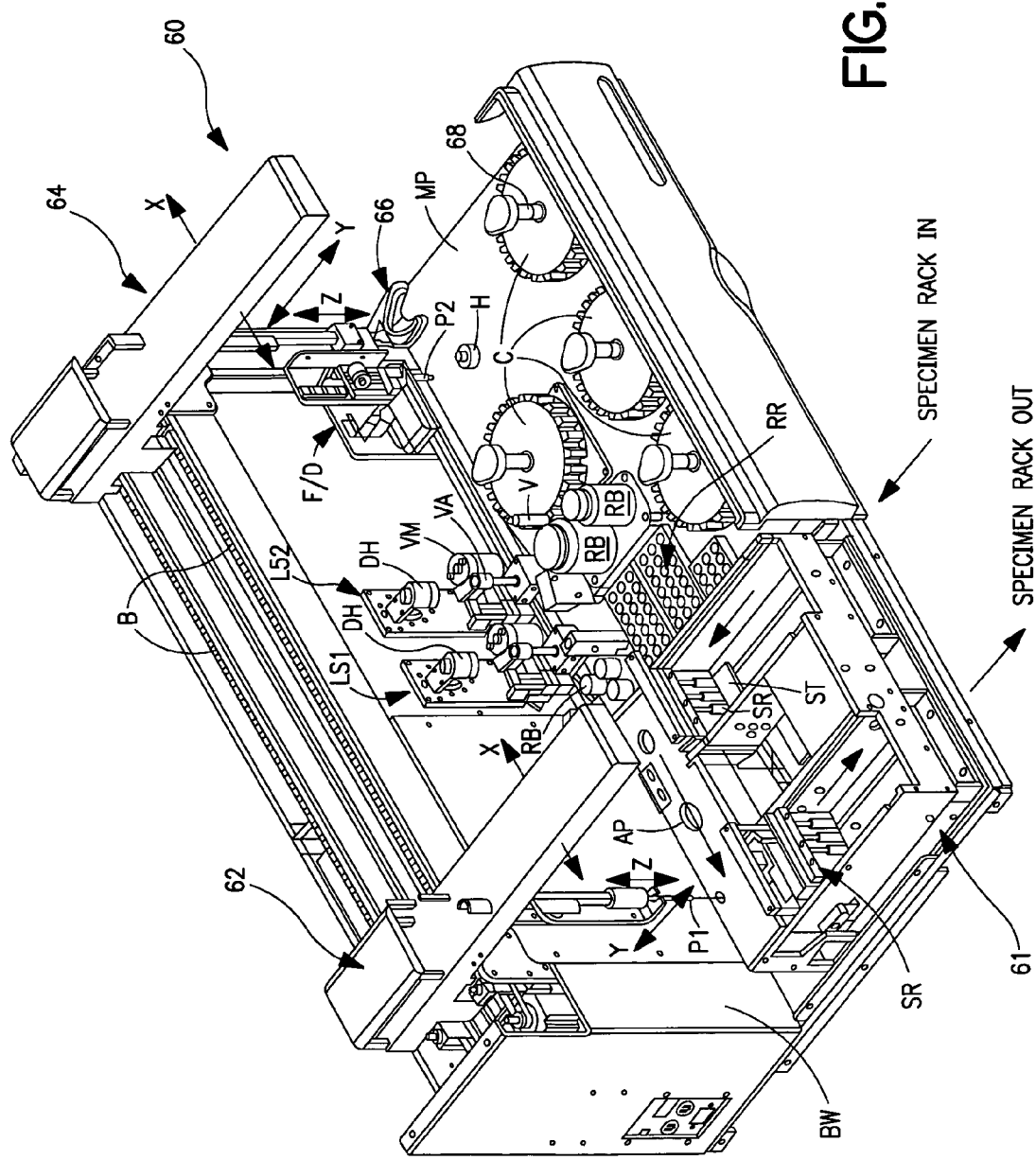
FIG. 22 is a perspective view of a preferred single platform instrument adapted to automatically carry out the sample preparation methods of the invention.

Referring to FIG. 22, a single platform instrument 60 adapted to automatically carry out the methods of FIGS. 2A and 2B is shown in perspective with its outer protective cover removed. As shown, instrument 60 is basically an expanded version of the above-mentioned PrepPlus2 instrument to render it capable of washing cell samples on-board. Like the PrepPlus2 instrument, instrument 60 includes a belt-driven X/Y/Z arm 62 that moves, under the control of three, microprocessor-controlled stepper motors, in a plane above the instrument's mech plate MC to control the X/Y/Z position of a pipetting probe P1. Depending on its position, probe P1 will dip into various reagents (in reagent bottles RB or reagent racks RR) specimen tubes ST or reaction vessels V to aspirate or dispense precise volumes of liquid in accordance with a sample preparation program being carried out. Being a higher throughput instrument than the PrePlus2 instrument, instrument 60 further includes a specimen transport station 61 for receiving a plurality of linear racks SR of specimen tubes (typically five or more tubes per rack) and for transporting such racks, one at a time, along a "U-shaped" path along which each tube is located at an aspiration position AP at which its contents are accessible to probe P1 for aspiration. As shown, the specimen tube rack enters from the "Specimen Rack In" position and moves rearwardly towards the back wall BW of the instrument. At the end of this travel, the specimen moves parallel to the back wall (from right to left, as viewed in the drawing), positioning each tube for aspiration. Finally, the specimen rack moves outwardly from the back wall towards the "Specimen Rack Out" position.

The mech plate of instrument 60 is adapted to support a plurality of tube carousels C, each being rotatably mounted on a hub H. There is one more hub than the number of carousels, whereby the carousels can be moved to different positions within the instrument to facilitate pipetting operations. Movement of the carousels is effected by a second X/Y/Z arm 64, which is also driven by a belt drive B and controlled by three stepper motors. Arm 64 operates to control the X/Y/Z position of a clamp 66 that serves to engage the vertically-extending handle 68 on each carousel for the purpose of lifting the carousel off its hub and transporting the carousel to another hub in an X/Y plane.

An additional feature of instrument 60 is a pair of lysing stations LS1 and LS2 mounted on the rear wall of the instrument. Upon having a reaction vessel V presented to its dispensing head DH, each station is adapted to inject a lysing solution into the reaction vessel followed by a quenching solution that terminates the red cell-lysing process. Timing, of course, is controlled by the instrument's internal microprocessor. Each lysing station includes a vortex mixer VM having an actuator VA that engages the vessel bottom and imparts an appropriate motion to effect mixing of the lyse and quench solutions with the cell sample. Transport of a reaction vessel from a carousel to the lysing station is achieved by the same clamp 66 used to transport carousels within the instrument. As shown, clamp 66 has a narrow back portion that opens and closes to engage and release the top portion of a reaction vessel.

As noted above, a very significant feature of instrument 60 is its ability to wash cell samples on-board at any time during their preparation cycle to rid the sample of interferants, etc. Apparatus for providing this feature is mounted on the rear wall of the instrument and is designated F/D. It includes an aspirating probe P2 which moves only vertically to enter and exit a reaction vessel presented to it by arm 64 and clamp 66. The cell washing apparatus includes a hollow fiber cartridge, as described above, and the essential hardware and software found in the CellPrep cell-washing instrument for washing cells by the hollow fiber technology. Being a self-contained pipetting and cell washing instrument, instrument 60 affords certain space cost-saving advantages vis-a-vis modular instrument systems of the above type.

The invention has been described with reference to particularly preferred embodiments. It will be apparent that many variations are possible without departing from the spirit of the invention. Accordingly, the scope of the invention should be determined not by the embodiments described, but by the appended claims and their legal equivalents.

What is claimed is:

1. A method for preparing a biological cell sample for detection of intracellullar components selected from the group consisting of: cytokines, tubulin filaments, intermediate filaments, defensins, effectors, cytokeratins, actins, B-cell antigen receptor complexes, proliferation antigens, enzymes, and apoptotic proteins, said method comprising the steps of:
   (a) dispensing a predetermined volume of a biological cell sample into a reaction vessel, said cell sample containing cells of interest comprising a selected one of said intracellular components;

(b) fixing said cells of interest, permeabilizing said cells of interest, and staining said selected one of said intracellular components by tagging said selected intracellular component with a fluorochrome-labeled antibody specific to said selected intracellular component, said fixing, permeabilizing and staining steps being carried out without any intervening washing step to rid said cell sample of interferants that could interfere with the detection of said selected intracellular component; and (c) washing said cell sample only after carrying out said fixing, permeabilizing and stain steps of step (b) to minimize the presence of said interferants.

2. The method as defined by claim 1 wherein said washing step is accomplished by filtering said cell sample through a semi-permeable membrane that selectively retains those cells of interest containing fluorochrome-tagged intracellular components and passes interferants.

3. The method as defined by claim 1 wherein said semi-permeable membrane is in the form of a hollow fiber into which the cell sample is drawn.

4. The method as defined by claim 1 wherein said washing step is accomplished by a centrifugation process.

5. The method as defined by claim 1 wherein step (b) further comprises the step of staining surface antigens on said cells of interest within said reaction vessel.

6. The method as defined by claim 5 wherein said step of staining surface antigens is carried out before said fixing step.

7. The method as defined by claim 1 wherein said tagging step is carried out before said fixing step.

8. The method as defined by claim 1 wherein said tagging step of staining said intracellular molecules of interest is carried out after said fixing step.

9. The method as defined by claim 1 wherein said biological cell sample comprises whole blood containing red blood cells, and wherein step (b) further comprises lysing said red cells to substantially eliminate said red cells from said biological cell sample.

10. The method as defined by claim 1 wherein said biological cell sample is selected from the group consisting of whole blood, purified cell lines, tumor cells, tissue and bone marrow.

11. The method as defined by claim 1 wherein said biological cell sample contains protein transport inhibitor.

12. The method as defined by claim 1 wherein said detection of intracellular components is to be performed on a flow cytometer.

* * * * *